United States Patent [19]
Sato et al.

[11] Patent Number: 5,342,546
[45] Date of Patent: Aug. 30, 1994

[54] 1,4-SUBSTITUTED DIHYDROBENZENE DERIVATIVES

[75] Inventors: Hisato Sato; Tomijiro Naito, both of Tokyo; Yasunobu Tuji, Sayama, all of Japan

[73] Assignees: L.C.C. Consultants Co., Ltd.; Citizen Watch Co., Ltd., both of Tokyo, Japan

[21] Appl. No.: 888,634

[22] Filed: May 27, 1992

[51] Int. Cl.$^5$ .................... C09K 19/06; C09K 19/52; G02F 1/13
[52] U.S. Cl. .................... 252/299.6; 252/299.01; 359/103
[58] Field of Search .................... 252/299.01, 299.63, 252/299.66, 299.67; 359/103

[56] References Cited

U.S. PATENT DOCUMENTS 4,505,837  3/1985  Römer et al. .................... 252/299.6
5,084,204  1/1992  Reiffenrath et al. ............ 252/299.62

FOREIGN PATENT DOCUMENTS 3006666  9/1981  Fed. Rep. of Germany .
WO88/07523  10/1988  PCT Int'l Appl. .

OTHER PUBLICATIONS

Tetrahedron vol. 29, pp. 3797–3806, 1973, Marvell et al. "Triene Electrocyclization's some structure reactivity reaction's".
Chimia, vol. 43, No. 12, 1989, pp. 382–385, U. Lauk, "Synthese Von Partiell Hydrierten 2-Phenylnaphthalimen Mit Nematischer Mesophase".
Journal of Organic Chemistry, vol. 43, No. 15, 1978, pp. 3068–3069, L. A. Levy, "Synthesis of Unsymmetrical Biphenyls via Aryl-Substituted 1,4–Cyclohexadienes".
Tetrahedron Letters, vol. 28, No. 29, 1987, pp. 3361–3362, I. Matsuda, et al., "Cyclo-Codimer of 1,3-Butadiene Derivatives With Non-Activated Terminal Acetylenes Catalyzed by Cationic Rhodium(I) Complex".
Journal of Organic Chemistry, vol. 46, No. 18, 1981, pp. 3721–3727, I. L. Reich, et al., "Synt Chlorinated and Brominated Biphenyl Oxides".
Chemische Berichte, vol. 114, No. 3, 1981, pp. 1027–1047, W. Eberbach et al., "Synthese, The Und Photolyse Substituierter 3,4–Epoxy-Cycloalkene".
Journal of the American Chemical Society, vol. 112, No. 23, 1990, pp. 8388–8398 R. D. Rieke, et al., "Synthesis of 4-Alkyl-4-(4-Methoxphenyl)Cyclohex-2-en-1-Ones and 5-Alkyl-5 3-Cyclohexadienes From Bis(Tricarbonylchromium)-Coordinated Bephenyls".

*Primary Examiner*—Shean Wu
*Attorney, Agent, or Firm*—Oblon, Spivak, Mcclelland, Maier & Neustadt

[57] ABSTRACT

Particular 1,4-substituted dihydrobenzene derivatives are useful as liquid crystalline materials. They are represented by the following formula (I):

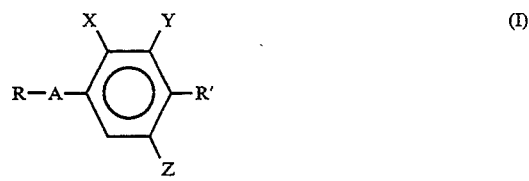

wherein A means a 1,4-dihydrophenylene group, R denotes a hydrogen atom or an alkyl or trans-4-alkylcyclohexyl group, R' represents a hydrogen or halogen atom, a trifluoromethyl, trifluoromethoxy, cyano, alkyl, alkoxyl or carboxyl group or a group —COO—B—R'' in which B stands for an unsubstituted or halogen-substituted 1,4-phenylene or 1,4-cyclohexenylene group and R'' represents a halogen atom or a cyano, alkyl or alkoxyl group, and X, Y and Z individually mean a hydrogen or halogen atom.

2 Claims, 4 Drawing Sheets

1,4-SUBSTITUTED DIHYDROBENZENE DERIVATIVES

BACKGROUND OF THE INVENTION

1) Field of the Invention

This invention relates to liquid crystalline compounds, and more specifically to liquid crystalline compounds useful as liquid crystalline display materials. The present invention is also concerned with liquid crystal compositions containing the liquid crystalline compounds and also with liquid crystal displays using the compositions.

2) Description of the Related Art

Liquid crystal displays making use of the electrooptical effects of a liquid crystal have found widespread utility in various equipment led by watches, clocks and handheld calculators and including word processors and television sets. In particular, TN (twisted nematic) liquid crystal displays using the optical anisotropy and dielectric anisotropy of a liquid crystalline substance are employed predominantly.

Characteristics which are now considered to be needed for a liquid crystal usable in a practical liquid crystal display are as follows:

(1) The liquid crystal has a broad liquid crystalline temperature range.

(2) The liquid crystal has low viscosity. It is evident that the response characteristics of a liquid crystal display have a close relationship with the viscosity of its liquid crystalline material. Described specifically, use of a low-viscosity liquid crystalline material is essential for the provision of a high response speed.

(3) Its optical anisotropy ($\Delta n$) conforms with the optical characteristics of the liquid crystal display. The quality of displayed images, such as the visual angle characteristic and contrast of images displayed by the liquid crystal display, are significantly governed by $\Delta n$, so that $\Delta n$ must be suitably controlled in order to obtain high contrast and high visual angle.

(4) Its dielectric anisotropy ($\Delta \epsilon$) conforms with the panel drive method. In the TN type, for example, $\Delta \epsilon$ must be large to permit a low drive voltage.

(5) The liquid crystal is stable chemically and optically.

No single liquid crystalline compound has been found yet, which can meet all the above requirements in characteristics. It is, therefore, the current circumstances that liquid crystal compositions formed in combination of several liquid crystalline compounds and/or non-liquid crystalline compounds having various characteristics are furnished for actual use.

Conventionally, liquid crystalline compounds have been classified depending on the compounds present in their core portions. Many compounds have been developed and actually employed including, for example, compounds containing benzene as a core, compounds with cyclohexane as a core, compounds having cyclohexene as a core, compounds having pyrimidine as a core, compounds with dioxane as a core, and compounds containing two or more of these moieties as a core. Even if they are used in combinations, it is still impossible to fully satisfy the above characteristics. There is accordingly a long standing demand for the provision of liquid crystalline compounds of a newer type.

SUMMARY OF THE INVENTION

With a view toward obtaining liquid crystalline compounds having excellent characteristics, the present inventors have synthesized numerous compounds and have investigated their liquid crystalline characteristics from various facets. As a result, it has been found that compounds containing dihydrobenzene in their core portions can satisfy the above requirements and are hence excellent as components for liquid crystals, leading to the completion of the present invention.

In one aspect of the present invention, there is thus provided a 1,4-substituted dihydrobenzene derivative represented by the following formula (I):

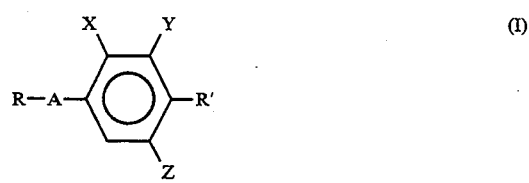

wherein A means a 1,4-dihydrophenylene group, R denotes a hydrogen atom or an alkyl or trans-4-alkylcyclohexyl group, R' represents a hydrogen or halogen atom, a trifluoromethyl, trifluoromethoxy, cyano, alkyl, alkoxyl or carboxyl group or a group —COO—B—R", said B standing for an unsubstituted or halogen-substituted 1,4-phenylene or 1,4-cyclohexenylene group and said R" representing a halogen atom or a cyano, alkyl or alkoxyl group, and X, Y and Z individually mean a hydrogen or halogen atom.

In another aspect of this invention, there is also provided a liquid crystal composition comprising the above 1,4-substituted dihydrobenzene derivative (I).

In a further aspect of this invention, there is also provided a liquid crystal display comprising a combination of cells opposing each other, each of said cells being composed of a transparent plate and transparent electrodes formed thereon, and a liquid crystal composition composed of the 1,4-substituted dihydrobenzene derivative (I) and sealed between the cells.

In the 1,4-substituted dihydrobenzene derivative (I), preferred examples of the alkyl group represented by each of R and R' include those having 1–10 carbon atoms whereas examples of the halogen atom represented by each of R', X an Y include fluorine, chlorine and bromine atoms.

It is well known that the drive voltage for a liquid crystal display now available on the market has a close relationship with the threshold voltage $V_{th}$ and also that the threshold voltage $V_{th}$ is in inverse proportional to the $\frac{1}{2}$nd power of the dielectric anisotropy $\Delta \epsilon$. Namely, liquid crystal compositions with positive dielectric anisotropy $\Delta \epsilon$ are used in liquid crystal displays. The threshold voltage does not increase substantially if a liquid crystal composition is prepared from liquid crystalline compounds having positive dielectric anisotropy $\Delta \epsilon$. There is hence a demand for liquid crystalline compounds having positive dielectric anisotropy $\Delta \epsilon$.

Although the response speed of a liquid crystal display is dependent most predominantly on the panel gap d, lower viscosity is also desired for the liquid crystalline material in order to achieve quicker response. The rise time $t_{on}$ upon impression of a voltage and the fall time $t_{off}$ upon cut-off of the voltage can be expressed by the following formulae, respectively:

$$t_{on} = n_{ii}d^2 (\epsilon_o \Delta \epsilon V^2 - K\pi^2)^{-1},$$

$$t_{off} = n_{ii}d^2/\pi^2 K$$

where $K = K_{11} + (K_{33} - 2K_{22})/4$, $n_{ii}$: viscosity parameter, and $\Delta\epsilon$: dielectric anisotropy.

Low-viscosity liquid crystalline compounds are therefore indispensable for the preparation of a liquid crystal composition which can realize a still higher response speed.

Further, liquid crystal compositions which are actually employed are each prepared generally by mixing a compound having a liquid crystalline phase around room temperature and another compound having a liquid crystalline phase in a temperature range higher than room temperature. To permit outdoor use of a liquid crystal display, a liquid crystalline phase must exist stably over a temperature range of from $-40°$ C. to $90°$ C. In addition, the dielectric anisotropy and anisotropy have temperature dependency, namely, vary abruptly around the N-I (nematic phase-isotropic liquid transition temperature) point. Liquid crystalline materials having a high N-I point are therefore required.

Where the phenyl core moiety of the compound (I) of this invention, said core moiety being represented by:

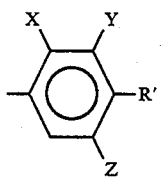

is an electron-attracting group, the compound (I) exhibits positive dielectric anisotropy $\Delta\epsilon$.

For example, 1-pentyl-4-(4-fluorophenyl)dihydrobenzene has positive $\Delta\epsilon$, shows a monotropic, nematic phase and has low viscosity, so that it can be combined with other liquid crystalline mixtures to provide low-viscosity liquid crystalline compositions.

Further, 1-(trans-4-pentylcyclohexyl)-4-(4-fluorophenyl)dihydrobenzene also has positive $\Delta\epsilon$, shows a broad liquid crystalline temperature range of from $74°$ C. to $159°$ C. and has low viscosity. It can therefore be combined with other liquid crystalline mixtures to provide low-viscosity liquid crystal compositions having a broad liquid crystalline temperature range.

Where the phenyl core moiety is an electron donating group, on the other hand, it is possible to obtain a compound which exhibits a broad liquid crystalline temperature range and has low viscosity.

For example, 1-(trans-4-propylcyclohexyl)-4-(4-methylphenyl)dihydrobenzene has a significantly broad liquid crystalline temperature range with a C-S point (crystal-smectic phase transition temperature) at $60°$ C., an S-N point (smectic phase-nematic phase transition temperature) at $118°$ C. and an N-I point at $190°$ C., and also has low viscosity. It can therefore be combined with other liquid crystalline mixtures to provide low-viscosity liquid crystalline compositions having a broad liquid crystalline temperature range.

Moreover, the compound (I) of this invention has high mutual solubility with a wide range of liquid crystalline substances so that it can be used, as a component for liquid crystal compositions, in combination with such a wide range of liquid crystalline substances. The compound (I) is therefore extremely useful for the improvement of their characteristics.

DETAILED DESCRIPTION OF THE INVENTION AND PREFERRED EMBODIMENTS

Figure 1:
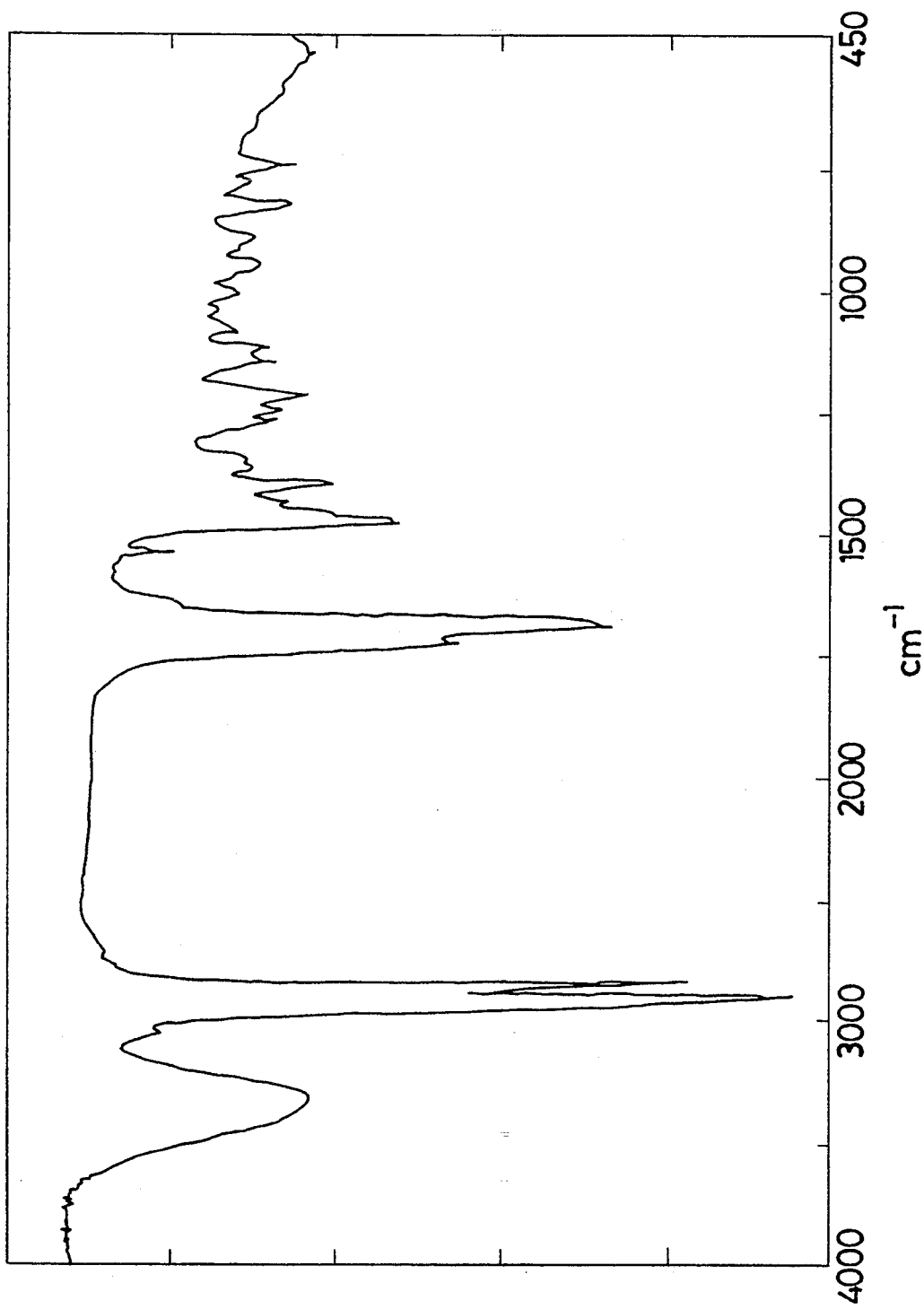
FIG. 1 is an infrared absorption spectrum of 4-pentylcyclohexenone obtained in Reference Example 1.

The 1,4-substituted dihydrobenzene derivative (I) of this invention can be prepared, for example, in accordance with the following processes.

In the case of the compounds of the formula (I) in which Z is a hydrogen or fluorine atom and R' is a hydrogen or halogen atom [Compound (Ia)], they can each be synthesized, for example, in accordance with the following reaction scheme, namely, by first reacting the Grignard reagent (III) with the p-substituted cyclohexenone (II) to form the 1-hydroxy-4-substituted cyclohexene derivative (IV) and then subjecting the derivative to dehydration.

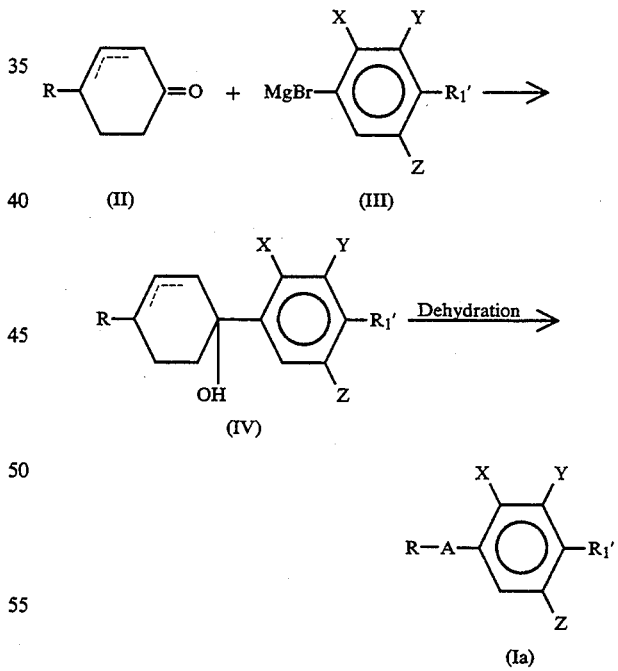

wherein $R'_1$ represents a hydrogen or halogen atom, A, R, X, Y and Z have the same meanings as defined above, and each dashed line indicates the existence of an extra bond along one of the corresponding adjacent C—C bonds and, hence, a double bond there and the absence of any extra bond along the other C—C bond and, thus, a single bond there.

The reaction between the compound (II) and the compound (III) can be conducted, for example, in an ether solvent such as anhydrous ethyl ether or tetrahydrofuran under conditions for general Grignard reactions.

After the completion of the reaction, dilute hydrochloric acid, a saturated aqueous solution of ammonium chloride or the like is added to the reaction mixture to hydrolyze the reaction product. The resulting hydrolysate is then extracted with diethyl ether or the like, washed with water and dried. The solvent is then distilled off so that the compound (IV) is obtained.

The compound (IV) obtained as described above is then dehydrated with p-toluenesulfonic acid or the like in an inert solvent such as toluene. After the reaction product is washed with water and dried, the solvent is distilled off under reduced pressure. The residue is then subjected to purification, for example, to recrystallization by using a polar solvent such as methanol, whereby the compound (I) of the present invention can be obtained.

The compound (II), the starting raw material for the above process, is a novel compound. It can be prepared, for example, in accordance with the following reaction scheme, namely, by causing the Grignard reagent (VI) to act on the monoketal cyclohexanone (V), subjecting the resultant compound (VII) to dehydration to form the 4-substituted cyclohexenone ketal (VIII) and then decomposing the ketal.

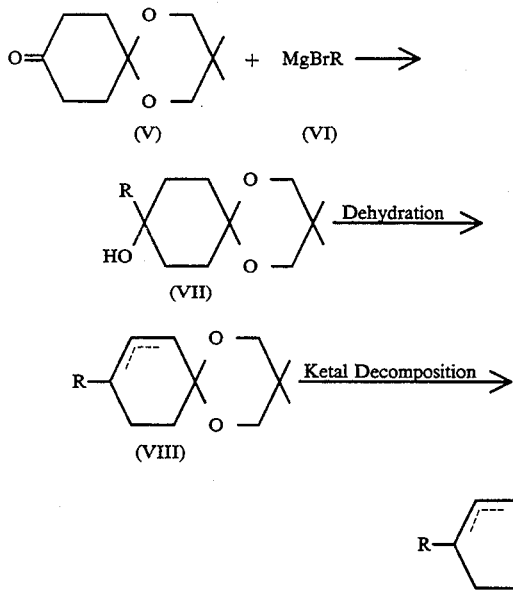

Among the compounds (VI), the compounds in which R is an alkyl group can each be prepared from the corresponding alkyl bromide. The compounds (VI) in which R is a trans-4-alkylcyclohexyl group can each be prepared from the corresponding trans-4-alkylcyclohexyl bromide which has been obtained by reacting phosphorus tribromide or the like with the corresponding trans-4-alkylcyclohexanol.

In the formula (VIII), R and the dashed line have the same meanings as defined above.

The reaction between the compound (V) and the compound (VI) can be practiced, for example, in an ether solvent such as anhydrous ether or tetrahydrofuran.

The compound (VII) can be prepared by hydrolyzing the reaction mixture with a saturated aqueous solution of ammonium chloride or the like, extracting the hydrolysate with a solvent such as diethyl ether, washing the extract with water and drying the same, and then distilling off the solvent from the extract under reduced pressure.

Further, the compound (VIII) can be obtained by causing, for example, potassium hydrogensulfate or the like to act on the compound (VII), which has been obtained as described above, in an inert solvent such as toluene to dehydrate the same, washing the resultant dehydration product with water and drying the same, and then distilling off the solvent under reduced pressure.

The compound (VIII) obtained as described above can be converted into the compound (II) by hydrolyzing the compound (VIII) with a strong acid such as hydrochloric acid, sulfuric acid or fluoroacetic acid in an inert solvent such as benzene or toluene, washing the hydrolyzate with water and drying the same, distilling off the solvent under reduced pressure, and then purifying the residue by a conventional method such as distillation or recrystallization.

Incidentally, a compound represented by the following formula (II'):

wherein R'' means a group formed by eliminating one hydrogen atom from the group R other than hydrogen is also formed as a byproduct together with the compound (II). This compound (II') can also be used as a raw material for the production of the compound of this invention. It is therefore unnecessary to separate it out.

The compounds (I) in which Z is a fluorine atom and R' is a carboxyl group [Compounds (Ib)] can each be obtained in accordance with the following reaction scheme, namely, by reacting the compound (Ia), which contains a fluorine atom at each of the 3- and 5-positions and a hydrogen atom at the 4-position [Compound (Ia')], with n-butyllithium to synthesize the compound (IX) and then reacting the compound (IX) with solid $CO_2$:

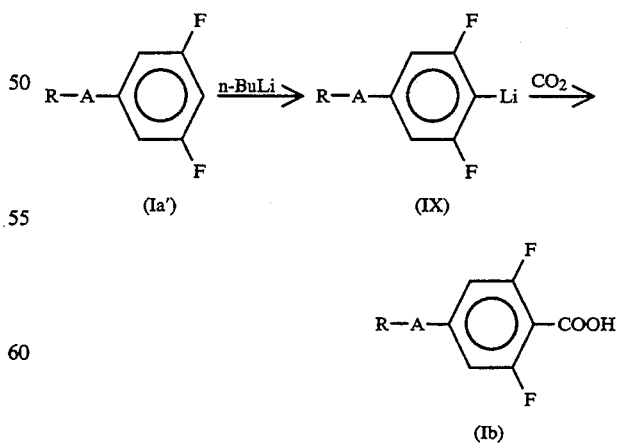

wherein R and A have the same meanings as defined above.

The above reaction can be practiced, for example, by adding a hexane solution of n-butyllithium to the compound (Ia) in an ether solvent such as tetrahydrofuran, adding solid CO$_2$ and then a dilute aqueous solution of hydrochloric acid, washing the reaction mixture with water, drying the thus-washed reaction mixture, distilling off the solvent under reduced pressure, and then purifying the residue by recrystallization or the like.

The compounds (I), in which Z is a fluorine atom and R' is a cyano group [Compounds (Ic)], can each be prepared in accordance with the following formula, namely, by successively reacting thionyl chloride, ammonia and thionyl chloride in this order with the compound (Ib). Each compound (Ic) can therefore be obtained via the corresponding benzoyl chloride and benzamide.

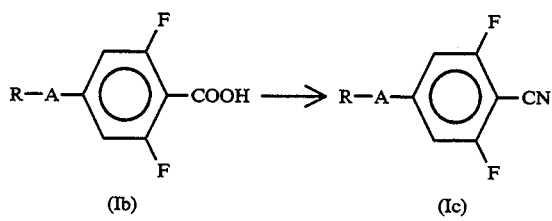

wherein R and A have the same meanings as defined above.

The above reaction can be practiced by dissolving the compound (Ib) in thionyl chloride and refluxing the resultant solution, distilling off the thionyl chloride under reduced pressure, adding aqueous ammonia and collecting precipitated crystals, and then purifying the crystals by recrystallization or the like to obtain the benzamide. After the benzamide is dissolved further in thionyl chloride and the resulting solution is refluxed, the thionyl chloride is distilled off under reduced pressure and the residue is then purified by recrystallization or the like.

The compounds (I), in which Z is a fluorine atom and R' is an alkyl group [Compounds (Id)], can each be obtained by causing potassium tert-butoxide and the corresponding alkyl iodide on the compound (IX) in accordance with the following reaction formula:

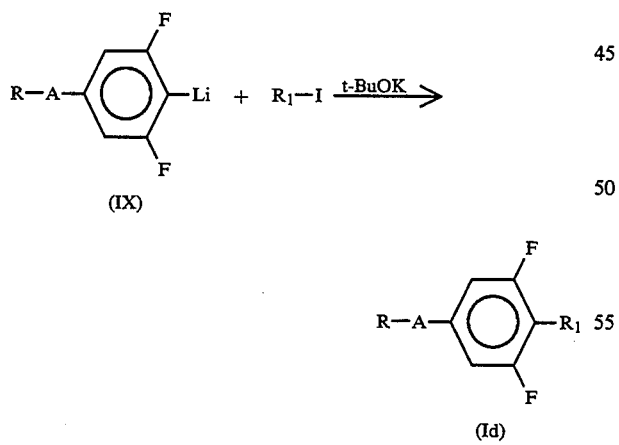

wherein R$_1$ means an alkyl group, and R and A have the same meanings as defined above.

The above reaction can be practiced, for example, by adding the tert-butoxide and alkyl iodide to the compound (IX) in an ether solvent such as tetrahydrofuran and, after the completion of the reaction, adding a dilute aqueous solution of hydrochloric acid and a saturated aqueous solution of sodium hydrogensulfite to the reaction mixture, washing the resulting reaction mixture with a saturated aqueous solution of sodium carbonate and then with water, drying the reaction mixture, distilling off the solvent under reduced pressure, and then purifying the residue by recrystallization or the like.

The compounds (I), in which Z is a fluorine atom and R' is an alkoxy group [Compounds (Ie)] can each be obtained in accordance with the following reaction scheme. Namely, sulfuric acid and sodium nitride are first with the compound (Ib) to synthesize the compound (X). Sulfuric acid and sodium nitrite are then reacted with the compound (X) to provide the diazonium salt (XI), followed by hydrolysis. The alkyl bromide (XII) is then reacted with the hydrolysate to obtain the corresponding compound (Ie).

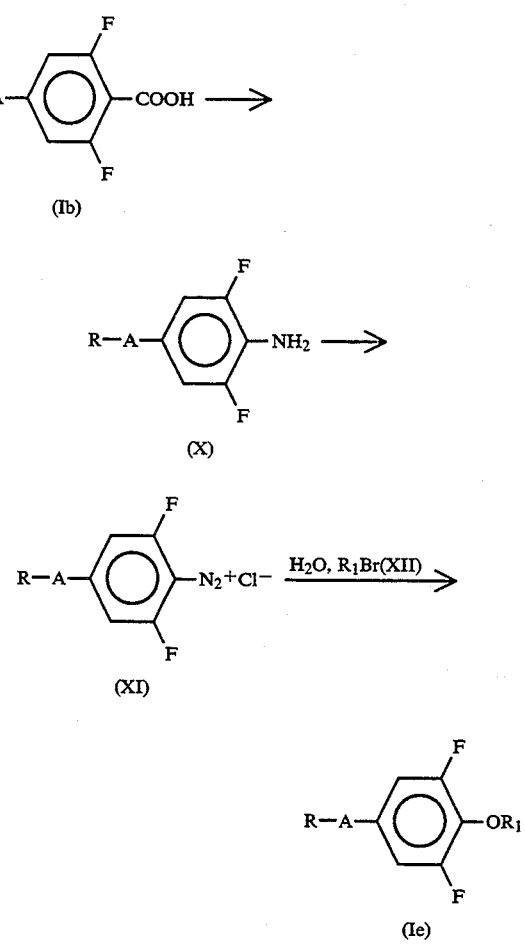

wherein R$_1$ means an alkyl group, and R and A have the same meanings as defined above.

The compounds (I), in which Z is a fluorine atom and R' is a group —COO—B—R" [Compounds (If)], can each be prepared in accordance with the following reaction formula, namely, by causing the 4-substituted phenol derivative or 4-substituted cyclohexanol (XIII) to act on the compound (Ib) and hence esterifying the latter.

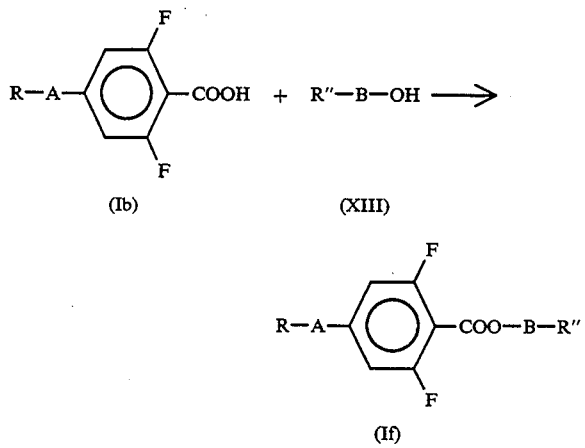

wherein R, R″, A and B have the same meanings as defined above.

Examples of the 4-substituted phenol derivative include 4-alkylphenols, 4-cyanophenol, 4-fluorophenol, 4-alkoxyphenols, 3-fluoro-4-cyanophenol, 3-chloro-4-cyanophenol, 3,4-difluorophenol, and 3,5-difluoro-4cyanophenol, whereas examples of the 4-substituted cyclohexanol include 4-alkylcyclohexanols.

The reaction between the compound (Ib) and the compound (XIII) can be practiced, for example, by conducting an esterification reaction in the presence of an esterifying agent such as N,N-dicyclohexylcarbodiimide in a solvent such as methylene chloride, filtering off crystals precipitated after the completion of the reaction, purifying the filtrate by column chromatography or the like, and then distilling off the solvent.

In each compound (I) of the invention prepared as described above, the dihydrophenyl group represented by A is obtained as a mixture of the below-described isomers because the starting raw material contains isomers and the positions of the double bonds may change during or after the reaction. The former two are principal isomers.

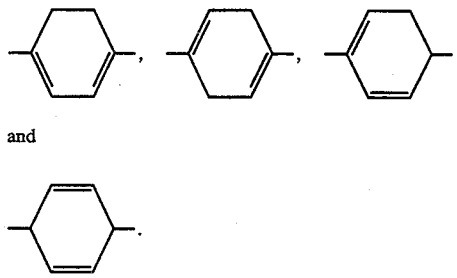

and

It is, however, to be noted that no practical problem whatsoever would arise from the use of the liquid crystalline compound as a mixture of such isomers. These isomers can be isolated by a known separation and purification method, for example, by liquid chromatography or the like.

The results of a comparison in properties as liquid crystals between certain compounds of this invention obtained as described above and other liquid crystalline compounds are summarized in Table 1.

Liquid Crystalline Compounds Tested

Invention Liquid Crystal 1

1-pentyl-4-(4-fluorophenyl)dihydrobenzene

Comparative Liquid Crystal 1

1-pentyl-4-(4-fluorophenyl)benzene

Comparative Liquid Crystal 2

1-pentyl-4-(4-fluorophenyl)cyclohexane

Comparative Liquid Crystal 3

1-pentyl-4-(4-fluorophenyl)-1-cyclohexene

Invention Liquid Crystal 2

1-(trans-4-pentylcyclohexyl)-4-(4-fluorophenyl)-dihydrobenzene

Comparative Liquid Crystal 4

1-(trans-4-pentylcyclohexyl)-4-(4-fluorophenyl)-benzene

Comparative Liquid Crystal 5

1-(trans-4-pentylcyclohexyl)-4-(4-fluorophenyl)-cyclohexane

Comparative Liquid Crystal 6

1-(trans-4-pentylcyclohexyl)-4-(4-fluorophenyl)-1-cyclohexene

Invention Liquid Crystal 3

1-(trans-4-pentylcyclohexyl)-4-(3,4-difluorophenyl)-dihydrobenzene

Comparative Liquid Crystal 7

1- (trans-4-pentylcyclohexyl) -4- (3,4-difluorophenyl)benzene

Comparative Liquid Crystal 8

1-(trans-4-pentylcyclohexyl)-4-(3,4-difluorophenyl)-cyclohexane

Comparative Liquid Crystal 9

1-(trans-4-pentylcyclohexyl)-4-(3,4-difluorophenyl)-1-cyclohexene

TABLE 1

| Liquid crystalline compounds tested | Temperature (°C.) | | | |
|---|---|---|---|---|
| | C | S | N | I |
| Invention liquid crystal 1 | 20 | — | | (6) |
| Comparative liquid crystal 1 | 43 | (34) | | |
| Comparative liquid crystal 2 | 34 | — | | — |
| Comparative liquid crystal 3 | 13 | — | | (−3) |
| Invention liquid crystal 2 | 74 | — | | 159 |
| Comparative liquid crystal 4 | 96 | — | | 154 |
| Comparative liquid crystal 5 | 66 | 75 | | 145 |
| Comparative liquid crystal 6 | 58 | — | | 145 |
| Invention liquid crystal 3 | 34 | — | | 121 |
| Comparative liquid crystal 7 | 45 | — | | 125 |
| Comparative liquid crystal 8 | 55 | — | | 108 |
| Comparative liquid crystal 9 | 30 | — | | 119 |

As is apparent from the results presented in Table 1, the compounds (I) according to the present invention have a broader nematic liquid crystalline temperature range than the conventional liquid crystalline compounds so that the former can be used advantageously, as components for TN liquid crystal composition, in combination with other liquid crystalline substances.

The compounds (I) according to the present invention can be used in combination with many known liquids crystalline compounds of liquid crystal compositions. Examples of such liquid crystalline compounds or liquid crystal include the liquid crystalline compounds represented by the following formulae, respectively, and liquid crystal compositions thereof.

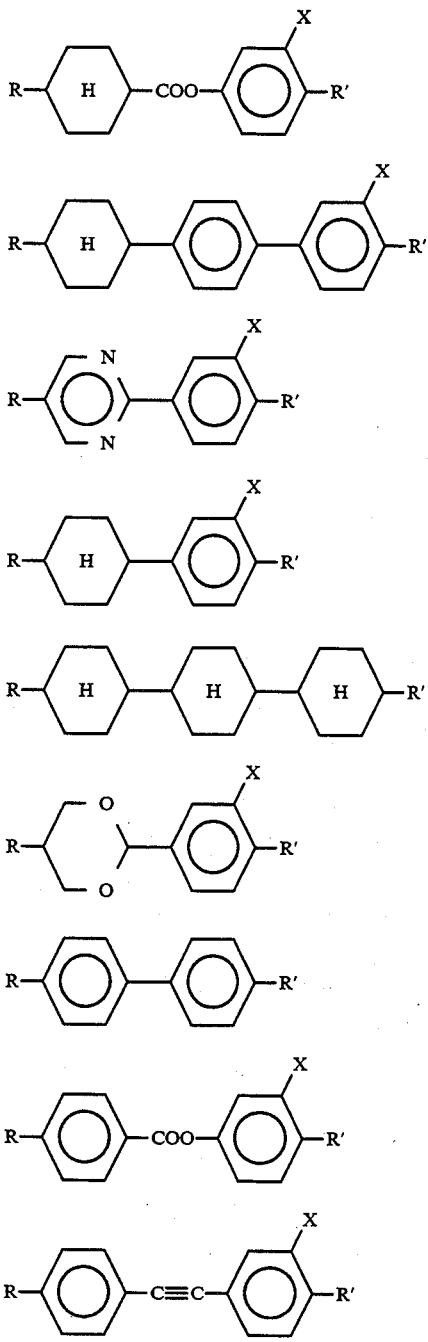

wherein R means a hydrogen atom or an alkyl group, R' denotes a halogen atom or an alkyl, alkoxy or cyano group, and X stands for a hydrogen or halogen atom.

The present invention will next be described in detail by the following examples and referential examples. It should however be borne in mind that this invention is by no means limited to or by the examples.

REFERENTIAL EXAMPLE 1

A solution of 60.4 g of pentyl bromide in 200 ml of anhydrous diethyl ether was added dropwise under stirring at 15°–20° C. to 11.5 g of magnesium metal powder, followed by reaction at room temperature for 1 hour so that pentyl magnesium bromide was formed. After 66 g of 1,4-cyclohexanedione-(2,2-dimethyl-1,3-dipropylene) monoketal were added dropwise at −10° to 0° C. to the thus-formed Grignard reagent, they were reacted at room temperature for additional 1 hour. After the completion of the reaction, 500 ml of a saturated aqueous solution of ammonium chloride (hereinafter referred to as "saturated NH₄Cl") were gradually added dropwise, followed by extraction with diethyl ether. After the extract was washed with a saturated aqueous solution of sodium chloride (hereinafter referred to as "saturated NaCl"), anhydrous sodium sulfate was added to dry the extract. The resultant mixture was filtered and the solvent was distilled off from the filtrate under reduced pressure, whereby 4-pentyl-4-hydroxycyclohexanone-(2,2-dimethyl-1,3-dipropylene) ketal was obtained as a crude reaction product.

The crude reaction product was dissolved in 200 ml of toluene. After 0.7 g of potassium hydrogensulfate was added to the resultant solution, the mixture thus obtained was refluxed under stirring. During the reflux, water which was formed by the reaction was removed by a decanter. The dehydration reaction was conducted for 23 hours and the reaction mixture was then cooled. The toluene layer was washed successively with a saturated aqueous solution of sodium carbonate (hereinafter referred to as "saturated Na₂CO₃") and then with saturated NaCl, and was then dried over anhydrous sodium sulfate. The toluene was thereafter distilled off under reduced pressure. The reaction product so obtained was recrystallized from n-hexane, and crystals were filtered off. The filtrate was passed through a silica gel column to purify the same. The n-hexane was then distilled off under reduced pressure, whereby 44 g of 4-pentylcyclohexenone-(2,2-dimethyl-1,3-dipropylene) ketal were obtained.

The compound so obtained was next dissolved in 40 ml of diethyl ether, followed by the dropwise addition of the resulting solution under stirring at −10° to 0° C. into a solution consisting of 88 ml of trifluoroacetic acid and 8.8 ml of water. They were thereafter reacted for 2 hours. After the completion of the reaction, saturated Na₂CO₃ was added until the reaction mixture became neutral. The diethyl ether layer was washed with saturated NaCl and then dried over anhydrous sodium sulfate. The diethyl ether was distilled off under reduced pressure. The residue was next purified by distillation under reduced pressure, whereby 16 g of 4-pentylcyclohexenone were obtained.

An infrared absorption spectrum of the 4-pentylcyclohexenone so obtained is shown in FIG. 1.

REFERENTIAL EXAMPLE 2

To a mixture of 104 g of phosphorus tribromide and 5 drops of a 48% aqueous solution of hydrogen bromide, 138 g of trans-4-pentylcyclohexanol were added dropwise under stirring while the temperature was controlled below 10° C. After the completion of the dropwise addition, the reaction mixture was reacted for one hour at the same temperature and then at room temperature for additional 1 hour. After the completion of the reaction, the reaction mixture was added with 200 ml of water, followed by extraction with diethyl ether. After the extract was washed with saturated NaCl, anhydrous sodium sulfate was added to dry the extract. The resultant mixture was filtered and the solvent was distilled off from the filtrate under reduced pressure, whereby trans-4-pentylcyclohexyl bromide was obtained.

In a similar manner to Referential Example 1 except for the replacement of 60.4 g of pentyl bromide by 91 g of the resultant trans-4-pentylcyclohexyl bromide, 20 g of 4-(trans-4-pentylcyclohexyl)cyclohexenone were obtained.

Figure 2:
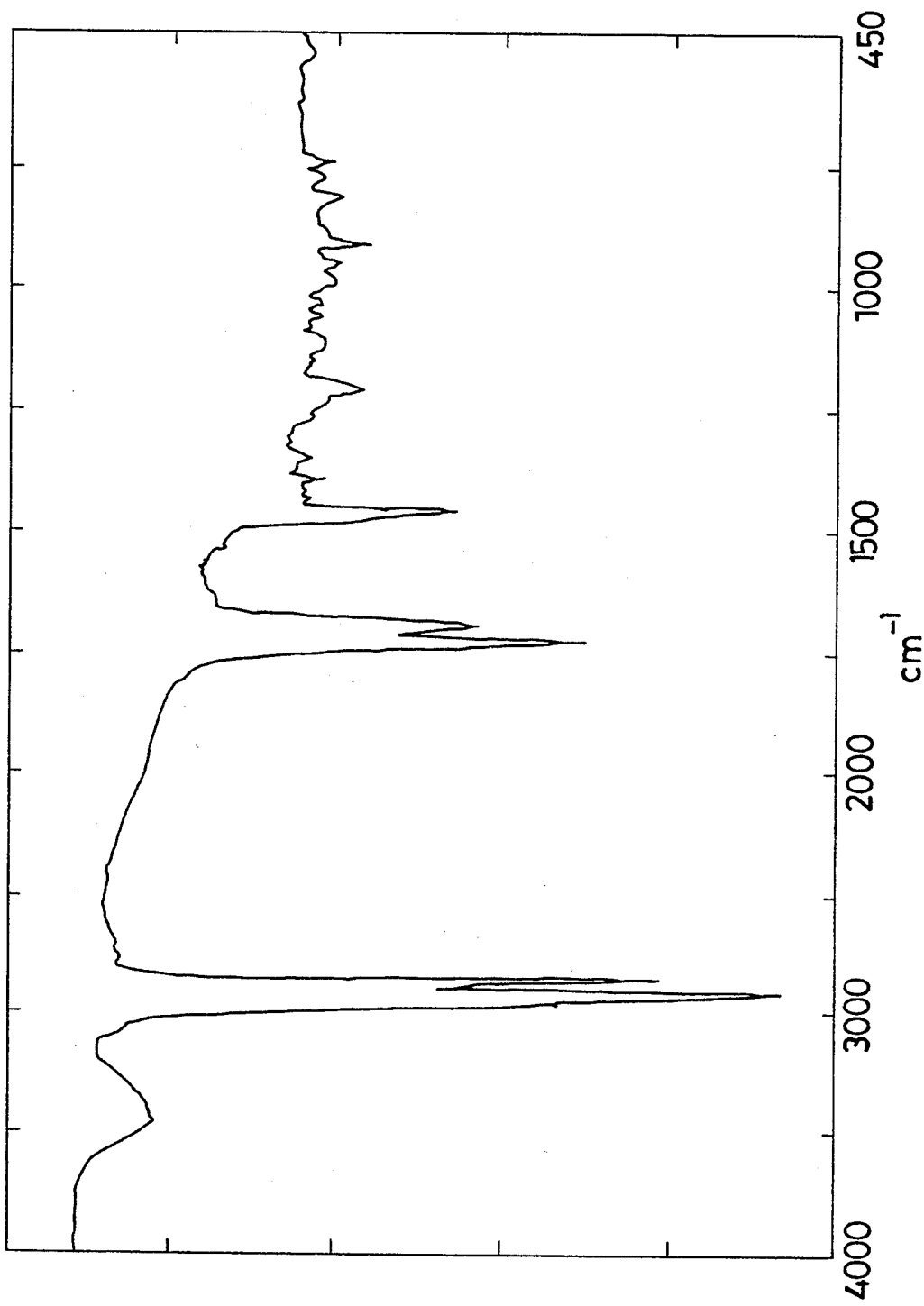
FIG. 2 is an infrared absorption spectrum of 4-(trans-4-pentylcyclohexyl) cyclohexenone obtained in Referential Example 2.

An infrared absorption spectrum of the 4-(trans-4-pentylcyclohexyl)cyclohexenone so obtained is shown in FIG. 2.

EXAMPLE 1

A solution of 6.3 g of 4-fluorobromobenzene in 20 ml of anhydrous diethyl ether was added dropwise under stirring at 15-20° C. to 1 g of magnesium metal powder, followed by reaction at room temperature for 1 hour so that a Grignard reagent was formed. After 5 g of the 4-pentylcyclohexenone obtained in Referential Example 1 were added under stirring at −10° to 0° C. to the thus-formed Grignard reagent, they were reacted at room temperature for additional 1 hour. After the completion of the reaction, diluted hydrochloric acid was added dropwise, followed by the extraction of the reaction mixture with diethyl ether. After the extract was washed with saturated NaCl, anhydrous sodium sulfate was added to dry the extract. The diethyl ether was distilled off under reduced pressure, whereby 4-(4-fluorophenyl)-4-hydroxy-1-pentylcyclohexene was obtained as a crude reaction product.

The crude reaction product was dissolved in 50 ml of toluene. After 0.1 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated $Na_2CO_3$ and then with saturated NaCl, and was then dried over anhydrous sodium sulfate. The toluene was thereafter distilled off under reduced pressure. The reaction product so obtained was recrystallized from ethanol, whereby 1 g of 1-pentyl-4-(4-fluorophenyl)dihydrobenzene was obtained.

The compound was a monotropic liquid crystal having a melting point of 20° C. and an I-N point of 6° C.

As a result of its fractionation and isolation by a high-performance liquid chromatography and its analysis by a nuclear magnetic resonance spectrometer (NMR), the compound was identified to consist primarily of the following two isomers:

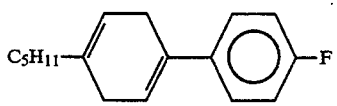

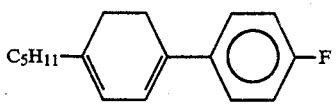

Figure 3:
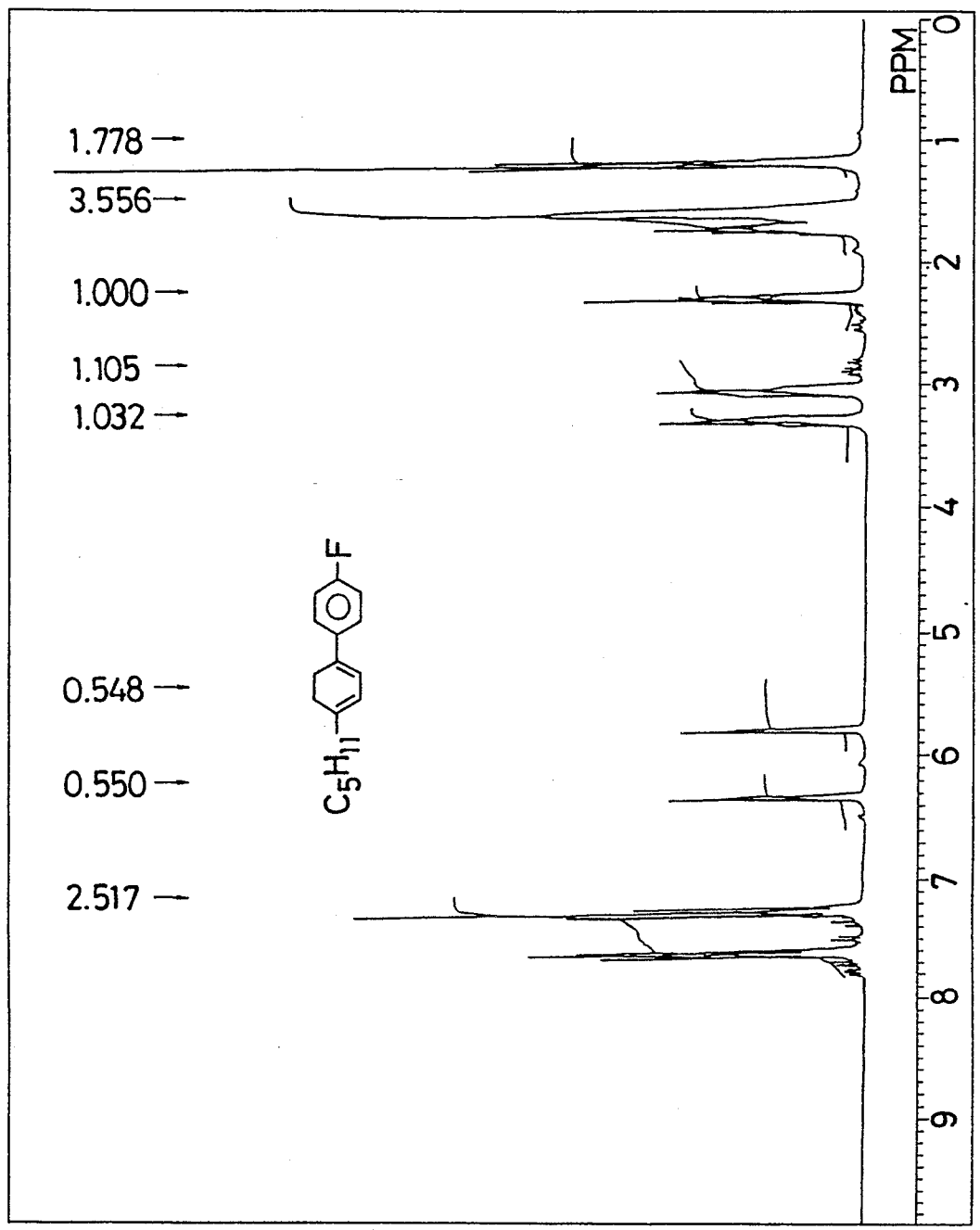
FIG. 3 is an NMR spectrum of one of isomers of 1-pentyl-4-(4-fluorophenyl)dihydrobenzene.
Figure 4:
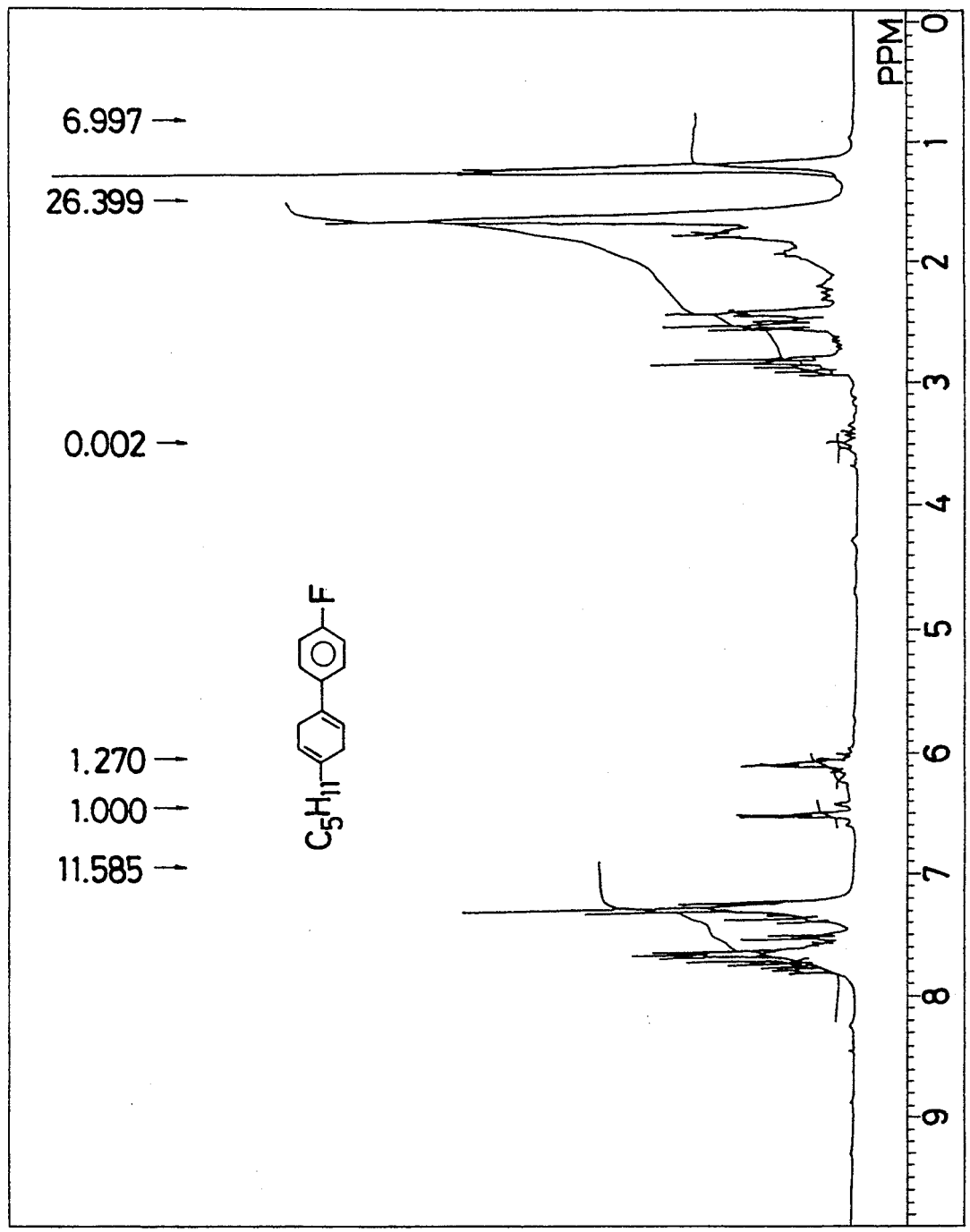
FIG. 4 is an NMR spectrum of another one of the isomers of 1-pentyl-4-(4-fluorophenyl)dihydrobenzene.

Their NMR spectra are shown in FIGS. 3 and 4.

EXAMPLE 2

In a similar manner to Example 1 except for the replacement of 5 g of 4-pentylcyclohexenone, one of the raw materials in Example 1, by 5.9 g of 4-heptylcyclohexenone, 1.5 g of 1-heptyl-4-(4-fluorophenyl)dihydrobenzene were obtained. Its melting point was 29° C.

The following compounds can also be prepared in a similar manner to Example 1.

1-Methyl-4-(4-fluorophenyl)dihydrobenzene
1-Ethyl-4-(4-fluorophenyl)dihydrobenzene
1-Propyl-4-(4-fluorophenyl)dihydrobenzene
1-Butyl-4-(4-fluorophenyl)dihydrobenzene
1-Hexyl-4-(4-fluorophenyl)dihydrobenzene
1-Octyl-4-(4-fluorophenyl)dihydrobenzene
1-Nonyl-4-(4-fluorophenyl)dihydrobenzene
1-Decyl-4-(4-fluorophenyl)dihydrobenzene

EXAMPLE 3

A solution of 8.0 g of 4-trifluoromethylbromobenzene in 30 ml of anhydrous diethyl ether was added dropwise under stirring at 15°-20° C. to 1 g of magnesium metal powder, followed by reaction at room temperature for 1 hour so that a Grignard reagent was formed. After 5 g of 4-pentylcyclohexenone was added under stirring at −10° to 0° C. to the thus-formed Grignard reagent, they were reacted at room temperature for additional 1 hour. After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 4-(4-trifluoromethylphenyl)-4-hydroxy-1-pentylcyclohexene was obtained as a crude reaction product.

The crude reaction product was dissolved in 80 ml of toluene. After 0.1 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated $Na_2CO_3$ and then with saturated NaCl, and was then dried over anhydrous sodium sulfate. The toluene was thereafter distilled off under reduced pressure. The reaction product so obtained was recrystallized from ethanol, whereby 1.2 g of 1-pentyl-4-(4-trifluoromethylphenyl)dihydrobenzene were obtained.

The compound so obtained had a melting point of 54° C.

The following compounds can also be prepared in a similar manner.

1-Methyl-4-(4-trifluoromethylphenyl)dihydrobenzene
1-Ethyl-4-(4-trifluoromethylphenyl)dihydrobenzene
1-Propyl-4-(4-trifluoromethylphenyl)dihydrobenzene
1-Butyl-4-(4-trifluoromethylphenyl)dihydrobenzene
1-Hexyl-4-(4-trifluoromethylphenyl)dihydrobenzene
1-Heptyl-4-(4-trifluoromethylphenyl)dihydrobenzene
1-Octyl-4-(4-trifluoromethylphenyl)dihydrobenzene
1-Nonyl-4-(4-trifluoromethylphenyl)dihydrobenzene
1-Decyl-4-(4-trifluoromethylphenyl)dihydrobenzene

EXAMPLE 4

A solution of 7.1 g of 3,4-difluorobromobenzene in 25 ml of anhydrous diethyl ether was added dropwise under stirring at 15°-20° C. to 1 g of magnesium metal powder, followed by reaction at room temperature for 1 hour so that a Grignard reagent was formed. After 5 g of 4-pentylcyclohexenone were added under stirring at −10° to 0° C. to the thus-formed Grignard reagent, they were reacted at room temperature for additional 1 hour. After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 4-(3,4-difluorophenyl)-4-hydroxy-1-pentylcyclohexene was obtained as a crude reaction product.

The crude reaction product was dissolved in 70 ml of toluene. After 0.1 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated $Na_2CO_3$ and then with saturated NaCl, and was then dried over anhydrous sodium sulfate. The toluene was thereafter distilled off under reduced pressure. The reaction product so obtained was purified by distillation, whereby 2 g of 1-pentyl-4-(3,4-difluorophenyl)dihydrobenzene were obtained.

The compound so obtained had a melting point of −31° C.

EXAMPLE 5

In a similar manner to Example 4 except for the replacement of 5 g of 4-pentylcyclohexenone, one of the raw materials in Example 4, by 6.3 g of 4-octylcyclohexenone, 2.2 g of 1-octyl-4-(3,4-difluorophenyl)-dihydrobenzene were obtained.

The compound so obtained had a melting point of 6° C.

The following compounds can also be prepared in a similar manner to Example 4.

1-Methyl-4-(3,4-difluorophenyl)dihydrobenzene
1-Ethyl-4-(3,4-difluorophenyl)dihydrobenzene
1-propyl-4-(3,4-difluorophenyl)dihydrobenzene
1-Butyl-4-(3,4-difluorophenyl)dihydrobenzene
1-Hexyl-4-(3,4-difluorophenyl)dihydrobenzene
1-Heptyl-4-(3,4-difluorophenyl)dihydrobenzene
1-Nonyl-4-(3,4-difluorophenyl)dihydrobenzene
1-Decyl-4-(3,4-difluorophenyl)dihydrobenzene

EXAMPLE 6

A solution of 7.1 g of 4-propylbromobenzene in 25 ml of anhydrous diethyl ether was added dropwise under stirring at 15°-20° C. to 1 g of magnesium metal powder, followed by reaction at room temperature for 1 hour so that a Grignard reagent was formed. After 5 g of 4-pentylcyclohexenone were added under stirring at −10° to 0° C. to the thus-formed Grignard reagent, they were reacted at room temperature for additional 1 hour. After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 4-(4-propylphenyl)-4-hydroxy-1-pentylcyclohexene was obtained as a crude reaction product.

The crude reaction product was dissolved in 70 ml of toluene. After 0.1 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated $Na_2CO_3$ and then with saturated NaCl, and was then dried over anhydrous sodium sulfate. The toluene was thereafter distilled off under reduced pressure. The reaction product so obtained was recrystallized from ethanol, whereby 0.8 g of 1-pentyl-4-(4-propylphenyl)dihydrobenzene was obtained.

The following compounds can also be prepared in a similar manner.

1-Methyl-4-(4-methylphenyl)dihydrobenzene
1-Methyl-4-(4-butylphenyl)dihydrobenzene
1-Methyl-4-(4-pentylphenyl)dihydrobenzene
1-Methyl-4-(4-octylphenyl)dihydrobenzene
1-Methyl-4-(4-decylphenyl)dihydrobenzene
1-Propyl-4-(4-methylphenyl)dihydrobenzene
1-Propyl-4-(4-butylphenyl)dihydrobenzene
1-Propyl-4-(4-pentylphenyl)dihydrobenzene
1-Propyl-4-(4-octylphenyl)dihydrobenzene
1-Propyl-4-(4-decylphenyl)dihydrobenzene
1-Hexyl-4-(4-methylphenyl)dihydrobenzene
1-Hexyl-4-(4-butylphenyl)dihydrobenzene
1-Hexyl-4-(4-pentylphenyl)dihydrobenzene
1-Hexyl-4-(4-octylphenyl)dihydrobenzene
1-Hexyl-4-(4-decylphenyl)dihydrobenzene
1-Octyl-4-(4-methylphenyl)dihydrobenzene
1-Octyl-4-(4-butylphenyl)dihydrobenzene
1-Octyl-4-(4-pentylphenyl)dihydrobenzene
1-Octyl-4-(4-octylphenyl)dihydrobenzene
1-Octyl-4-(4-decylphenyl)dihydrobenzene
1-Decyl-4-(4-methylphenyl)dihydrobenzene
1-Decyl-4-(4-butylphenyl)dihydrobenzene
1-Decyl-4-(4-pentylphenyl)dihydrobenzene
1-Decyl-4-(4-octylphenyl)dihydrobenzene
1-Decyl-4-(4-decylphenyl)dihydrobenzene

EXAMPLE 7

A solution of 6.5 g of p-bromoanisole in 20 ml of anhydrous diethyl ether was added dropwise under stirring at 15°-20° C. to 1 g of magnesium metal powder, followed by reaction at room temperature for 1 hour so that a Grignard reagent was formed. After 5 g of 4-pentylcyclohexenone were added under stirring at −10° to 0° C. to the thus-formed Grignard reagent, they were reacted at room temperature for additional 1 hour. After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 4-(4-methoxyphenyl)-4-hydroxy-1-pentylcyclohexene was obtained as a crude reaction product.

The crude reaction product was dissolved in 70 ml of toluene. After 0.1 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated $Na_2CO_3$ and then with saturated NaCl, and was then dried over anhydrous sodium sulfate. The toluene was thereafter distilled off under reduced pressure. The reaction product so obtained was recrystallized from ethanol, whereby 1.2 g of 1-pentyl-4-(4-methoxyphenyl) dihydrobenzene were obtained.

The compound so obtained had a melting point of 55° C.

The following compounds can also be prepared in a similar manner.

1-Methyl-4-(4-methoxyphenyl)dihydrobenzene
1-Methyl-4-(4-butoxyphenyl)dihydrobenzene
1-Methyl-4-(4-pentyloxyphenyl)dihydrobenzene
1-Methyl-4-(4-octyloxyphenyl)dihydrobenzene
1-Methyl-4-(4-decyloxyphenyl)dihydrobenzene
1-Propyl-4-(4-methoxyphenyl)dihydrobenzene
1-Propyl-4-(4-butoxyphenyl)dihydrobenzene
1-Propyl-4-(4-pentyloxyphenyl)dihydrobenzene
1-Propyl-4-(4-octyloxyphenyl)dihydrobenzene
1-Propyl-4-(4-decyloxyphenyl)dihydrobenzene
1-Hexyl-4-(4-methoxyphenyl)dihydrobenzene
1-Hexyl-4-(4-butoxyphenyl)dihydrobenzene
1-Hexyl-4-(4-pentyloxyphenyl)dihydrobenzene
1-Hexyl-4-(4-octyloxyphenyl)dihydrobenzene
1-Hexyl-4-(4-decyloxyphenyl)dihydrobenzene
1-Octyl-4-(4-methoxyphenyl)dihydrobenzene
1-Octyl-4-(4-butoxyphenyl)dihydrobenzene
1-Octyl-4-(4-pentyloxyphenyl)dihydrobenzene
1-Octyl-4-(4-octyloxyphenyl)dihydrobenzene
1-Octyl-4-(4 -decyloxyphenyl)dihydrobenzene
1-Decyl-4-(4 -methoxyphenyl)dihydrobenzene
1-Decyl-4-(4 -butoxyphenyl)dihydrobenzene
1-Decyl-4-(4 -pentyloxyphenyl)dihydrobenzene
1-Decyl-4-(4 -octyloxyphenyl)dihydrobenzene
1-Decyl-4-(4-decyloxyphenyl)dihydrobenzene

EXAMPLE 8

A solution of 8.5 g of p-dibromobenzene in 35 ml of anhydrous diethyl ether was added dropwise under stirring at 15°-20° C. to 1 g of magnesium metal powder, followed by reaction at room temperature for 1 hour so that a Grignard reagent was formed. After 5 g of 4-pentylcyclohexenone were added under stirring at −10° to 0° C. to the thus-formed Grignard reagent, they were reacted at room temperature for additional 1 hour. After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 4-(4-bromophenyl)-4-hydroxy-1-pentylcyclohexene was obtained as a crude reaction product.

The crude reaction product was dissolved in 80 ml of toluene. After 0.1 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated Na$_2$CO$_3$ and then with saturated NaCl, and was then dried over anhydrous sodium sulfate. The toluene was thereafter distilled off under reduced pressure. The reaction product so obtained was recrystallized from ethanol, whereby 1.5 g of 1-pentyl-4-(4-bromophenyl)dihydrobenzene were obtained.

The compound so obtained had a melting point of 74° C.

The following compounds can also be prepared in a similar manner.

1-Methyl-4-(4-bromophenyl)dihydrobenzene
1-Ethyl-4-(4-bromophenyl)dihydrobenzene
1-Propyl-4-(4-bromophenyl)dihydrobenzene
1-Butyl-4-(4-bromophenyl)dihydrobenzene
1-Hexyl-4-(4-bromophenyl)dihydrobenzene
1-Heptyl-4-(4-bromophenyl)dihydrobenzene
1-Octyl-4-(4-bromophenyl)dihydrobenzene
1-Nonyl-4- ( 4-bromophenyl)dihydrobenzene
1-Decyl-4 - ( 4 -bromophenyl)dihydrobenzene

EXAMPLE 9

In 15 ml of N,N-dimethylformamide, 4 g of the 1-pentyl-4-(4-bromophenyl)dihydrobenzene, which had been obtained in Example 8, were dissolved, followed by the addition of 1.4 g of cuprous cyanide. The resulting mixture was reacted for 6 hours at reflux temperature. After the completion of the reaction, aqueous ammonia was added to the reaction mixture, followed by the extraction of the reaction mixture with toluene. The extract was washed with aqueous ammonia and then with saturated NaCl. Anhydrous sodium sulfate was thereafter added to dry the extract. The toluene was distilled off under reduced pressure. The reaction product so obtained was recrystallized twice from ethanol, whereby 0.8 g of 1-pentyl-4-(4-cyanophenyl)dihydrobenzene was obtained.

The compound so obtained was a nematic liquid crystal having C-N and N-I points at 34° C. and 52° C., respectively.

The following compounds can also be prepared in a similar manner.

1-Methyl-4-(4-cyanophenyl)dihydrobenzene
1-Ethyl-4-(4-cyanophenyl)dihydrobenzene
1-Propyl-4-(4-cyanophenyl)dihydrobenzene
1-Butyl-4-(4-cyanophenyl)dihydrobenzene
1-Hexyl-4-(4-cyanophenyl)dihydrobenzene
1-Heptyl-4-(4-cyanophenyl)dihydrobenzene
1-Octyl-4-(4-cyanophenyl)dihydrobenzene
1-Nonyl-4-(4-cyanophenyl)dihydrobenzene
1-Decyl-4-(4-cyanophenyl)dihydrobenzene

EXAMPLE 10

A solution of 5.6 g of 4-fluorobromobenzene in 22 ml of anhydrous diethyl ether was added dropwise under stirring at 10°-15° C. to 0.66 g of magnesium metal powder, followed by reaction at room temperature for 1 hour so that a Grignard-reagent was formed. After 5 g of the trans-4-pentylcyclohexylcyclohexenone, which had been obtained in Referential Example 2, were added under stirring at −10° to 0° C. to the thus-formed Grignard reagent, they were reacted at room temperature for additional 1 hour. After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 1-(trans-4-pentylcyclohexyl)-4-(4-fluorophenyl)-4-hydroxy-cyclohexene was obtained as a crude reaction product.

The crude reaction product was dissolved in 50 ml of toluene. After 0.05 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated $Na_2CO_3$ and then with saturated NaCl, and was then dried over anhydrous sodium sulfate. The toluene was thereafter distilled off under reduced pressure. The reaction product so obtained was recrystallized twice from ethanol, whereby 1.0 g of 1-(trans-4-pentylcyclohexyl)-4-(4-fluorophenyl)dihydrobenzene was obtained.

The compound so obtained was a nematic crystal having C-N and N-I points at 74° C. and 159° C., respectively.

EXAMPLE 11

In a similar manner to Example 10 except for the replacement of trans-4-pentylcyclohexylcyclohexenone, one of the raw materials, by cyclohexylcyclohexenone, trans-4-ethylcyclohexylcyclohexenone, trans-4-propylcyclohexylcyclohexenone and trans-4-butylcyclohexylcyclohexenone, respectively, were obtained 1-cyclohexyl-4-(4-fluorophenyl) dihydrobenzene having a melting point of 78° C.; 1-(trans-4-ethylcyclohexyl)-4-(4-fluorophenyl)dihydrobenzene, a nematic liquid crystal having C-N and N-I points at 78° C. and 129° C., respectively; 1-(trans-4-propylcyclohexyl)-4-(4-fluorophenyl)dihydrobenzene, a nematic liquid crystal having C-N and N-I points at 80° C. and 160° C., respectively; and 1-(trans-4-butylcyclohexyl)-4-(4-fluorophenyl)dihydrobenzene, a nematic liquid crystal having C-N and N-I points at 88° C. and 156° C., respectively.

The following compounds can also be prepared in a similar manner.

1-(Trans-4-hexylcyclohexyl)-4-(4-fluorophenyl)dihydrobenzene
1-(Trans-4-heptylcyclohexyl)-4-(4-fluorophenyl)dihydrobenzene
1-(Trans-4-octylcyclohexyl)-4-(4-fluorophenyl)dihydrobenzene
1-(Trans-4-nonylcyclohexyl)-4-(4-fluorophenyl)dihydrobenzene
1-(Trans-4-decylcyclohexyl)-4-(4-fluorophenyl)dihydrobenzene

EXAMPLE 12

A solution of 6.0 g of 3,4-difluorobromobenzene in 25 ml. of anhydrous diethyl ether was added dropwise under stirring at 10°-15° C. to 0.66 g of magnesium metal powder, followed by reaction at room temperature for 1 hour so that a Grignard reagent was formed. After 5 g of trans-4-pentylcyclohexylcyclohexenone were added under stirring at −10° to 0° C. to the thus-formed Grignard reagent, they were reacted at room temperature for additional 1 hour. After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 1-(trans-4-pentylcyclohexyl)-4-(3,4-difluorophenyl)-4-hydroxy-cyclohexene was obtained as a crude reaction product.

The crude reaction product was dissolved in 60 ml of toluene. After 0.05 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated $Na_2CO_3$ and then with saturated NaCl, and was then dried over anhydrous sodium sulfate. The toluene was thereafter distilled off under reduced pressure. The reaction product so obtained was recrystallized twice from ethanol, whereby 12 g of 1-(trans-4-pentylcyclohexyl)-4-(3,4-difluorophenyl)dihydrobenzene were obtained.

The compound so obtained was a nematic liquid crystal having C-N and N-I points at 34° C. and 121° C., respectively.

EXAMPLE 13

In a similar manner to Example 12 except for the replacement of trans-4-pentylcyclohexylcyclohexenone, one of the raw materials, by trans-4-ethylcyclohexylcyclohexenone, trans-4-propylcyclohexylcyclohexenone and trans-4-butylcyclohexylcyclohexenone, respectively, were obtained 1-(trans-4-ethylcyclohexyl)-4-(3,4-difluorophenyl)dihydrobenzene, a nematic liquid crystal having C-N and N-I points at 32° C. and 67° C., respectively; 1-(trans-4-propylcyclohexyl)-4-(3,4-difluorophenyl)dihydrobenzene, a nematic liquid crystal having C-N and N-I points at 16° C. and 103° C., respectively; and 1-(trans-4-butylcyclohexyl)-4-(3,4-difluorophenyl)dihydrobenzene, a nematic liquid crystal having C-N and N-I points at 29° C. and 106° C., respectively.

The following compounds can also be prepared in a similar manner.

1-(Trans-4-hexylcyclohexyl)-4-(3,4-difluorophenyl)-dihydrobenzene
1-(Trans-4-heptylcyclohexyl)-4-(3,4-difluorophenyl)-dihydrobenzene
1-(Trans-4-octylcyclohexyl)-4-(3,4-difluorophenyl)-dihydrobenzene
1-(Trans-4-nonylcyclohexyl)-4-(3,4-difluorophenyl)-dihydrobenzene
1-(Trans-4-decylcyclohexyl)-4-(3,4-difluorophenyl)-dihydrobenzene

EXAMPLE 14

A solution of 6.1 g of 4-propylbromobenzene in 25 ml of anhydrous diethyl ether was added dropwise under stirring at 10°-15° C. to 0.66 g of magnesium metal powder, followed by reaction at room temperature for one hour so that a Grignard reagent was formed. After 5 g of trans-4-pentylcyclohexylcyclohexenone were added under stirring at −10° to 0° C. to the thus-formed Grignard reagent, they were reacted at room temperature for additional 1 hour. After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 1-(trans-4-pentylcyclohexyl)-4-(4-propylphenyl)-4-hydroxycyclohexene was obtained as a crude reaction product.

The crude reaction product was dissolved in 60 ml of toluene. After 0.05 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated $Na_2CO_3$ and then with saturated NaCl, and was then dried over anhydrous sodium sulfate. The toluene was thereafter distilled off under reduced pressure. The reaction product so obtained was recrystallized from ethanol, whereby 1.3 g of 1-(trans-4-pentylcyclohexyl)-4-(4-propylphenyl)dihydrobenzene were obtained.

The compound so obtained was a nematic liquid crystal having C-S, S-N and N-I points at 91° C., 154° C. and 250° C., respectively.

EXAMPLE 15

In a similar manner to Example 14 except for the replacement of 4-propylbromobenzene, one of the raw materials, by 4-methylbromobenzene and of trans-4-pentylcyclohexylcyclohexenone by trans-4-propylcyclohexylcyclohexenone, 1-(trans-4-propylcyclohexyl)-4-(4-methylphenyl)dihydrobenzene was obtained.

The compound so obtained was a liquid crystal having C-S, S-N and N-I points at 60° C., 118° C. and 190° C., respectively.

The following compounds can also be prepared in a similar manner to Example 14.

1-(Trans-4-methylcyclohexyl)-4-(4-methylphenyl)dihydrobenzene
1-(Trans-4-methylcyclohexyl)-4-(4-butylphenyl)dihydrobenzene
1-(Trans-4-methylcyclohexyl)-4-(4-pentylphenyl)dihydrobenzene
1-(Trans-4-methylcyclohexyl)-4-(4-octylphenyl)dihydrobenzene
1-(Trans-4-methylcyclohexyl)-4-(4-decylphenyl)dihydrobenzene
1-(Trans-4-propylcyclohexyl)-4-(4-butylphenyl)dihydrobenzene
1-(Trans-4-propylcyclohexyl)-4-(4-pentylphenyl)dihydrobenzene
1-(Trans-4-propylcyclohexyl)-4-(4-octylphenyl)dihydrobenzene
1-(Trans-4-propylcyclohexyl)-4-(4-decylphenyl)dihydrobenzene
1-(Trans-4-hexylcyclohexyl)-4-(4-methylphenyl)dihydrobenzene
1-(Trans-4-hexylcyclohexyl)-4-(4-butylphenyl)dihydrobenzene
1-(Trans-4-hexylcyclohexyl)-4-(4-Pentylphenyl)dihydrobenzene
1-(Trans-4-hexylcyclohexyl)-4-(4-octylphenyl)dihydrobenzene
1-(Trans-4-hexylcyclohexyl)-4-(4-decylphenyl)dihydrobenzene
1-(Trans-4-octylcyclohexyl)-4-(4-methylphenyl)dihydrobenzene
1-(Trans-4-octylcyclohexyl)-4-(4-butylphenyl)dihydrobenzene
1-(Trans-4-octylcyclohexyl)-4-(4-pentylphenyl)dihydrobenzene
1-(Trans-4-octylcyclohexyl)-4-(4-octylphenyl)dihydrobenzene
1-(Trans-4-octylcyclohexyl)-4-(4-decylphenyl)dihydrobenzene
1-(Trans-4-decylcyclohexyl)-4-(4-butylphenyl)dihydrobenzene
1-(Trans-4-decylcyclohexyl)-4-(4-pentylphenyl)dihydrobenzene
1-(Trans-4-decylcyclohexyl)-4-(4-octylphenyl)dihydrobenzene
1-(Trans-4-decylcyclohexyl)-4-(4-decylphenyl)dihydrobenzene

EXAMPLE 16

A solution of 5.8 g of 4-bromoanisole in 30 ml of anhydrous diethyl ether was added dropwise under stirring at 10°–15° C. to 0.66 g of magnesium metal powder, followed by reaction at room temperature for one hour so that a Grignard reagent was formed. After 5 g of trans-4-pentylcyclohexylcyclohexenone were added under stirring at −10° to 0° C. to the thus-formed Grignard reagent, they were reacted at room temperature for additional 1 hour. After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 1-(trans-4-pentylcyclohexyl)-4-(4-methoxyphenyl)-4-hydroxycyclohexene was obtained as a crude reaction product.

The crude reaction product was dissolved in 60 ml of toluene. After 0.05 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated $Na_2CO_3$ and then with saturated NaCl, and was then dried over anhydrous sodium sulfate. The toluene was thereafter distilled off under reduced pressure. The reaction product so obtained was recrystallized from ethanol, whereby 1.0 g of 1-(trans-4-pentylcyclohexyl)-4-(4-methoxyphenyl)dihydrobenzene was obtained.

The compound so obtained was a liquid crystal having C-S, S-N and N-I points at 84° C., 109° C. and 190° C., respectively.

The following compounds can also be prepared in a similar manner.

1-(Trans-4-methylcyclohexyl)-4-(4-methoxyphenyl)-dihydrobenzene
1-(Trans-4-methylcyclohexyl)-4-(4-butoxyphenyl)dihydrobenzene
1-(Trans-4-methylcyclohexyl)-4-(4-pentyloxyphenyl)-dihydrobenzene
1-(Trans-4-methylcyclohexyl)-4-(4-octyloxyphenyl)-dihydrobenzene 1-(Trans-4-methylcyclohexyl)-4-(4-decyloxyphenyl)-dihydrobenzene
1-(Trans-4-propylcyclohexyl)-4-(4-methoxyphenyl)-dihydrobenzene
1-(Trans-4-propylcyclohexyl)-4-(4-butoxyphenyl)dihydrobenzene
1-(Trans-4-propylcyclohexyl)-4-(4-pentyloxyphenyl)-dihydrobenzene
1-(Trans-4-propylcyclohexyl)-4-(4-octyloxyphenyl)-dihydrobenzene
1-(Trans-4-propylcyclohexyl)-4-(4-decyloxyphenyl)-dihydrobenzene
1-(Trans-4-hexylcyclohexyl)-4-(4-methoxyphenyl)dihydrobenzene
1-(Trans-4-hexylcyclohexyl)-4-(4-butoxyphenyl)dihydrobenzene
1-(Trans-4-hexylcyclohexyl)-4-(4-pentyloxyphenyl)-dihydrobenzene
1-(Trans-4-hexylcyclohexyl)-4-(4-octyloxyphenyl)dihydrobenzene
1-(Trans-4-hexylcyclohexyl)-4-(4-decyloxyphenyl)-dihydrobenzene
1-(Trans-4-octylcyclohexyl)-4-(4-methoxyphenyl)dihydrobenzene
1-(Trans-4-octylcyclohexyl)-4-(4-butoxyphenyl)dihydrobenzene
1-(Trans-4-octylcyclohexyl)-4-(4-pentyloxyphenyl)-dihydrobenzene
1-(Trans-4-octylcyclohexyl)-4-(4-octyloxyphenyl)dihydrobenzene
1-(Trans-4-octylcyclohexyl)-4-(4-decyloxyphenyl)dihydrobenzene
1-(Trans-4-decylcyclohexyl)-4-(4-methoxyphenyl)dihydrobenzene
1-(Trans-4-decylcyclohexyl)-4-(4-butoxyphenyl)dihydrobenzene
1-(Trans-4-decylcyclohexyl)-4-(4-pentyloxyphenyl)-dihydrobenzene
1-(Trans-4-decylcyclohexyl)-4-(4-octyloxyphenyl)dihydrobenzene
1-(Trans-4-decylcyclohexyl)-4-(4-decyloxyphenyl)-dihydrobenzene

EXAMPLE 17

A solution of 6.9 g of 4-trifluoromethylbromobenzene in 30 ml of anhydrous diethyl ether was added dropwise under stirring at 10°-15° C. to 0.66 g of magnesium metal powder, followed by reaction at room temperature for 1 hour so that a Grignard reagent was formed. After 5 g of trans-4-pentylcyclohexylcyclohexenone were added under stirring at −10° to 0° C. to the thus-formed Grignard reagent, they were reacted at room temperature for additional 1 hour. After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 1-(trans-4-pentylcyclohexyl)-4-(4-trifluoromethylphenyl)-4-hydroxycyclohexene was obtained as a crude reaction product.

The crude reaction product was dissolved in 80 ml of toluene. After 0.05 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated Na$_2$CO$_3$ and then with saturated NaCl, and was then dried over anhydrous sodium sulfate. The toluene was thereafter distilled off under reduced pressure. The reaction product so obtained was recrystallized from ethanol, whereby 1.4 g of 1-(trans-4-pentylcyclohexyl)-4-(4-trifluoromethylphenyl)dihydrobenzene were obtained.

The compound so obtained was a nematic liquid crystal having C-N and N-I points at 100° C. and 133° C., respectively.

The following compounds can also be prepared in a similar manner.

1-(Trans-4-methylcyclohexyl)-4-(4-trifluoromethylphenyl)dihydrobenzene
1-(Trans-4-ethylcyclohexyl)-4-(4-trifluoromethylphenyl)dihydrobenzene
1-(Trans-4-propylcyclohexyl)-4-(4-trifluoromethylphenyl)dihydrobenzene
1-(Trans-4-butylcyclohexyl)-4-(4-trifluoromethylphenyl)dihydrobenzene
1-(Trans-4-hexylcyclohexyl)-4-(4-trifluoromethylphenyl)dihydrobenzene
1-(Trans-4-heptylcyclohexyl)-4-(4-trifluoromethylphenyl)dihydrobenzene
1-(Trans-4-octylcyclohexyl)-4-(4-trifluoromethylphenyl)dihydrobenzene
1-(Trans-4-nonylcyclohexyl)-4-(4-trifluoromethylphenyl)dihydrobenzene
1-(Trans-4-decylcyclohexyl)-4-(4-trifluoromethylphenyl)dihydrobenzene

EXAMPLE 18

A solution of 7.2 g of p-dibromobenzene in 40 ml of anhydrous diethyl ether was added dropwise under stirring at 10°-15° C. to 0.66 g of magnesium metal powder, followed by reaction at room temperature for one hour so that a Grignard reagent was formed. After 5 g of trans-4-pentylcyclohexylcyclohexenone were added under stirring at −10° to 0° C. to the thus-formed Grignard reagent, they were reacted at room temperature for additional 1 hour. After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 1-(trans-4-pentylcyclohexyl)-4-(4-bromophenyl)-4-hydroxycyclohexene was obtained as a crude reaction product.

The crude reaction product was dissolved in 90 ml of toluene. After 0.05 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated Na$_2$CO$_3$ and then with saturated NaCl, and was then dried over anhydrous sodium sulfate. The toluene was thereafter distilled off under reduced pressure. The reaction product so obtained was recrystallized from ethanol, whereby 1.6 g of 1-(trans-4-pentylcyclohexyl)-4-(4-bromophenyl)dihydrobenzene were obtained.

The following compounds can also be prepared in a similar manner.

1-(Trans-4-methylcyclohexyl)-4-(4-bromophenyl)dihydrobenzene
1-(Trans-4-ethylcyclohexyl)-4-(4-bromophenyl)dihydrobenzene
1-(Trans-4-propylcyclohexyl)-4-(4-bromophenyl)dihydrobenzene
1-(Trans-4-butylcyclohexyl)-4-(4-bromophenyl)dihydrobenzene
1-(Trans-4-hexylcyclohexyl)-4-(4-bromophenyl)dihydrobenzene
1-(Trans-4-heptylcyclohexyl)-4-(4-bromophenyl)dihydrobenzene
1-(Trans-4-octylcyclohexyl)-4-(4-bromophenyl)dihydrobenzene
1-(Trans-4-nonylcyclohexyl)-4-(4-bromophenyl)dihydrobenzene
1-(Trans-4-decylcyclohexyl)-4-(4-bromophenyl)dihydrobenzene

EXAMPLE 19

In 20 ml of N,N-dimethylformamide, 7 g of the 1-(trans-4-pentylcyclohexyl)-4-(4-bromophenyl)dihydrobenzene, which had been obtained in Example 18, were dissolved, followed by the addition of 2.0 g of cuprous cyanide. The resulting mixture was reacted for 6 hours at reflux temperature. After the completion of the reaction, aqueous ammonia was added to the reaction mixture, followed by extraction with toluene. The extract was washed with aqueous ammonia and then with saturated NaCl. Anhydrous sodium sulfate was thereafter added to dry the extract. The toluene was distilled off under reduced pressure. The reaction product so obtained was recrystallized from ethanol, whereby 0.7 g of 1-(trans-4-pentylcyclohexyl)-4-(4-cyanophenyl)dihydrobenzene was obtained.

The following compounds can also be prepared in a similar manner.

1-(Trans-4-methylcyclohexyl)-4-(4-cyanophenyl)dihydrobenzene
1-(Trans-4-ethylcyclohexyl)-4-(4-cyanophenyl)dihydrobenzene
1-(Trans-4-propylcyclohexyl)-4-(4-cyanophenyl)dihydrobenzene
1-(Trans-4-butylcyclohexyl)-4-(4-cyanophenyl)dihydrobenzene
1-(Trans-4-hexylcyclohexyl)-4-(4-cyanophenyl)dihydrobenzene
1-(Trans-4-heptylcyclohexyl)-4-(4-cyanophenyl)dihydrobenzene
1-(Trans-4-octylcyclohexyl)-4-(4-cyanophenyl)dihydrobenzene
1-(Trans-4-nonylcyclohexyl)-4-(4-cyanophenyl)dihydrobenzene
1-(Trans-4-decylcyclohexyl)-4-(4-cyanophenyl)dihydrobenzene

EXAMPLE 20

A solution of 6.7 of 3-fluoro-4-chlorobromobenzene in 30 ml of anhydrous diethyl ether was added dropwise under stirring at 10°-15° C. to 0.66 g of magnesium metal powder, followed by reaction at room temperature for 1 hour so that a Grignard reagent was formed. After 4.8 g of trans-4-propylcyclohexylcyclohexenone were added under stirring at −10° to 0° C. to the thus-formed Grignard reagent, they were reacted at room temperature for additional 1 hour. After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 1-(trans-4-propylcyclohexyl)-4-(3-fluoro-4-chlorophenyl)-4-hydroxycyclohexene was obtained as a crude reaction product.

The crude reaction product was dissolved in 80 ml of toluene. After 0.05 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated $Na_2CO_3$ and then with saturated NaCl, and was then dried over anhydrous sodium sulfate. The toluene was thereafter distilled off under reduced pressure. The reaction product so obtained was recrystallized from ethanol, whereby 1.5 g of 1-(trans-4-propylcyclohexyl)-4-(3-fluoro-4-chlorophenyl)dihydrobenzene were obtained.

The compound so obtained was a nematic liquid crystal having C-N and N-I points at 48° C. and 156° C., respectively.

The following compounds can also be prepared in a similar manner.

1-(Trans-4-methylcyclohexyl)-4-(3-fluoro-4-chlorophenyl)dihydrobenzene
1-(Trans-4-ethylcyclohexyl)-4-(3-fluoro-4-chlorophenyl)dihydrobenzene
1-(Trans-4-pentylcyclohexyl)-4-(3-fluoro-4-chlorophenyl)dihydrobenzene
1-(Trans-4-butylcyclohexyl)-4-(3-fluoro-4-chlorophenyl)dihydrobenzene
1-(Trans-4-hexylcyclohexyl)-4-(3-fluoro-4-chlorophenyl)dihydrobenzene
1-(Trans-4-heptylcyclohexyl)-4-(3-fluoro-4-chlorophenyl)dihydrobenzene
1-(Trans-4-octylcyclohexyl)-4-(3-fluoro-4-chlorophenyl)dihydrobenzene
1-(Trans-4-nonylcyclohexyl)-4-(3-fluoro-4-chlorophenyl)dihydrobenzene
1-(Trans-4-decylcyclohexyl)-4-(3-fluoro-4-chlorophenyl)dihydrobenzene

EXAMPLE 21

A solution of 5.0 g of bromobenzene in 20 ml of anhydrous diethyl ether was added dropwise under stirring at 10°-15° C. to 0.66 g of magnesium metal powder, followed by reaction at room temperature for 1 hour so that a Grignard reagent was formed. After 5 g of trans-4-pentylcyclohexylcyclohexenone were added under stirring at −10° to 0° C. to the thus-formed Grignard reagent, they were reacted at room temperature for additional 1 hour. After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 1-(trans-4-pentylcyclohexyl)-4-phenyl-4-hydroxycyclohexene was obtained as a crude reaction product.

The crude reaction product was dissolved in 50 ml of toluene. After 0.05 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated Na$_2$CO$_3$ and then with saturated NaCl, and was then dried over anhydrous sodium sulfate. The toluene was thereafter distilled off under reduced pressure. The reaction product so obtained was recrystallized from ethanol, whereby 1.5 g of 1-(trans-4-pentylcyclohexyl)-4-phenyl-dihydrobenzene were obtained.

The compound so obtained was a liquid crystal having C-S, S-N and N-I points at 57° C., 76° C. and 106° C., respectively.

The following compounds can also be prepared in a similar manner.

1-(Trans-4-methylcyclohexyl)-4-phenyldihydrobenzene
1-(Trans-4-ethylcyclohexyl)-4-phenyldihydrobenzene
1-(Trans-4-propylcyclohexyl)-4-phenyldihydrobenzene
1-(Trans-4-butylcyclohexyl)-4-phenyldihydrobenzene
1-(Trans-4-hexylcyclohexyl)-4-phenyldihydrobenzene
1-(Trans-4-heptylcyclohexyl)-4-phenyldihydrobenzene
1-(Trans-4-octylcyclohexyl)-4-phenyldihydrobenzene
1-(Trans-4-nonylcyclohexyl)-4-phenyldihydrobenzene
1-(Trans-4-decylcyclohexyl)-4-phenyldihydrobenzene

EXAMPLE 22

A solution of 7.7 g of 4-trifluoromethoxybromobenzene in 30 ml of anhydrous diethyl ether was added dropwise under stirring at 10°–15° C. to 0.66 g of magnesium metal powder, followed by reaction at room temperature for 1 hour so that a Grignard reagent was formed. After 5 g of trans-4-pentylcyclohexylcyclohexenone were added under stirring at −10° to 0° C. to the thus-formed Grignard reagent, they were reacted at room temperature for additional 1 hour. After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 1-(trans-4-pentylcyclohexyl)-4-(4-trifluoromethoxyphenyl)-4-hydroxycyclohexene was obtained as a crude reaction product.

The crude reaction product was dissolved in 70 ml of toluene. After 0.05 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated Na$_2$CO$_3$ and then with saturated NaCl, and was then dried over anhydrous sodium sulfate. The toluene was thereafter distilled off under reduced pressure. The reaction product so obtained was recrystallized from ethanol, whereby 1.4 g of 1-(trans-4-pentylcyclohexyl)-4-(4-trifluoromethoxyphenyl)dihydrobenzene were obtained.

The compound so obtained was a liquid crystal having C-S, S-N and N-I points at 37° C., 102° C. and 138° C., respectively.

The following compounds Can also be prepared in a similar manner.

1-(Trans-4-methylcyclohexyl)-4-(4-trifluoromethoxyphenyl)dihydrobenzene
1-(Trans-4-ethylcyclohexyl)-4-(4-trifluoromethoxyphenyl)dihydrobenzene
1-(Trans-4-propylcyclohexyl)-4-(4-trifluoromethoxyphenyl)dihydrobenzene
1-(Trans-4-butylcyclohexyl)-4-(4-trifluoromethoxyphenyl)dihydrobenzene
1-(Trans-4-hexylcyclohexyl)-4-(4-trifluoromethoxyphenyl)dihydrobenzene
1-(Trans-4-heptanecyclohexyl)-4-(4-trifluoromethoxyphenyl)dihydrobenzene
1-(Trans-4-octanecyclohexyl)-4-(4-trifluoromethoxyphenyl)dihydrobenzene
1-(Trans-4-nonanecyclohexyl)-4-(4-trifluoromethoxyphenyl)dihydrobenzene
1-(Trans-4-decanecyclohexyl)-4-(4-trifluoromethoxyphenyl)dihydrobenzene

EXAMPLE 23

A solution of 6.0 g of 2,3-difluorobromobenzene in 25 ml of anhydrous diethyl ether was added dropwise under stirring at 10°–15° C. to 0.66 g of magnesium metal powder, followed by reaction at room temperature for one hour so that a Grignard reagent was formed. After 4.5 g of trans-4-propylcyclohexylcyclohexenone were added under stirring at −10° to 0° C. to the thus-formed Grignard reagent, they were reacted at room temperature for additional 1 hour. After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 1-(trans-4-propylcyclohexyl)-4-(2,3-difluorophenyl-4-hydroxycyclohexene was obtained as a crude reaction product.

The crude reaction product was dissolved in 60 ml of toluene. After 0.05 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated Na$_2$CO$_3$ and then with saturated NaCl, and was then dried over anhydrous sodium sulfate. The toluene was thereafter distilled off under reduced pressure. The reaction product so obtained was recrystallized from ethanol, whereby 1.1 g of 1-(trans-4-propylcyclohexyl)-4-(2,3-difluorophenyl)-dihydrobenzene were obtained.

The compound so obtained was a nematic liquid crystal having C-N and N-I points at 26° C. and 57° C., respectively.

EXAMPLE 24

In a similar manner to Example 23 except for the replacement of trans-4-propylcyclohexylhexenone, one of the raw materials in Example 23, by trans-4-butylcyclohexylcyclohexenone, 1-(trans-4-butylcyclohexyl)-4-(2,3-difluorophenyl)dihydrobenzene was obtained.

The compound so obtained was a nematic liquid crystal having C-N and N-I points at −1° C. and 24° C., respectively.

The following compounds can also be prepared in a similar manner to Example 23.

1-(Trans-4-methylcyclohexyl)-4-(2,3-difluorophenyl)-dihydrobenzene
1-(Trans-4-ethylcyclohexyl)-4-(2,3-difluorophenyl)-dihydrobenzene
1-(Trans-4-pentylcyclohexyl)-4-(2,3-difluorophenyl)-dihydrobenzene
1-(Trans-4-hexylcyclohexyl)-4-(2,3-difluorophenyl)-dihydrobenzene
1-(Trans-4-heptylcyclohexyl)-4-(2,3-difluorophenyl)-dihydrobenzene
1-(Trans-4-octylcyclohexyl)-4-(2,3-difluorophenyl)-dihydrobenzene
1-(Trans-4-nonylcyclohexyl)-4-(2,3-difluorophenyl)-dihydrobenzene
1-(Trans-4-decylcyclohexyl)-4-(2,3-difluorophenyl)-dihydrobenzene

EXAMPLE 25

In anhydrous tetrahydrofuran (30 ml), 2.8 g of the 1-(trans-4-propylcyclohexyl)-4-(2,3-difluorophenyl)-dihydrobenzene, which had been obtained in Example 23, were dissolved. The resulting solution was cooled to −70° C., to which 6 ml of a solution of nbutyllithium butyllithium in hexane (1.5 mol/l) were added dropwise. After the completion of the dropwise addition, the resulting mixture was reacted at −50° C. for additional 5 hours, whereby 1-(trans-4-propylcyclohexyl)-4-(2,3-difluoro-4-lithiumphenyl)dihydrobenzene was formed. The product so obtained was cooled to −70° C., to which a solution of 1.0 g of potassium tert-butoxide in 15 ml of anhydrous tetrahydrofuran was added dropwise under stirring over one hour. After the completion of the dropwise addition, the resulting mixture was stirred for 10 minutes at the same temperature, followed by the dropwise addition under stirring of a solution of 1.52 g of iodoethane in 5 ml of anhydrous tetrahydrofuran. After the completion of the dropwise addition, the resultant mixture was heated to room temperature under stirring and reacted. After the completion of the reaction, diluted hydrochloric acid was gradually added dropwise, followed by the extraction with diethyl ether. After the extract was washed successively with saturated NaHSO$_3$, saturated Na$_2$CO$_3$ and saturated NaCl, anhydrous sodium sulfate was added to dry the extract. The resultant mixture was filtered and the solvent was distilled off from the filtrate under reduced pressure. The reaction product was recrystallized from a mixed solvent of ethyl acetate and ethanol, whereby 2.0 g of 1-(trans-4-propylcyclohexyl)-4-(2,3-difluoro-4-ethylphenyl) dihydrobenzene were obtained.

The compound so obtained was a liquid crystal having C-S, S-N and N-I points at 0° C., 53° C. and 99° C., respectively.

The following compounds can also be prepared similar manner.

1-(Trans-4-methylcyclohexyl)-4-(2,3-difluoro-4-methylphenyl)dihydrobenzene
1-(Trans-4-methylcyclohexyl)-4-(2,3-difluoro-4-butylphenyl)dihydrobenzene
1-(Trans-4-methylcyclohexyl)-4-(2,3-difluoro-4-pentylphenyl)dihydrobenzene
1-(Trans-4-methylcyclohexyl)-4-(2,3-difluoro-4-octylphenyl)dihydrobenzene
1-(Trans-4-methylcyclohexyl)-4-(2,3-difluoro-4-decylphenyl)dihydrobenzene
1-(Trans-4-propylcyclohexyl)-4-(2,3-difluoro-4-methylphenyl)dihydrobenzene
1-(Trans-4-propylcyclohexyl)-4-(2,3-difluoro-4-butylphenyl)dihydrobenzene
1-(Trans-4-propylcyclohexyl)-4-(2,3-difluoro-4-pentylphenyl)dihydrobenzene
1-(Trans-4-propylcyclohexyl)-4-(2,3-difluoro-4-octylphenyl)dihydrobenzene
1-(Trans-4-propylcyclohexyl)-4-(2,3-difluoro-4-decylphenyl)dihydrobenzene
1-(Trans-4-hexylcyclohexyl)-4-(2,3-difluoro-4-methylphenyl)dihydrobenzene
1-(Trans-4-hexylcyclohexyl)-4-(2,3-difluoro-4-butylphenyl)dihydrobenzene
1-(Trans-4-hexylcyclohexyl)-4-(2,3-difluoro-4-pentylphenyl)dihydrobenzene
1-(Trans-4-hexylcyclohexyl)-4-(2,3-difluoro-4-octylphenyl)dihydrobenzene
1-(Trans-4-hexylcyclohexyl)-4-(2,3-difluoro-4-decylphenyl)dihydrobenzene
1-(Trans-4-octylcyclohexyl)-4-(2,3-difluoro-4-methylphenyl)dihydrobenzene
1-(Trans-4-octylcyclohexyl)-4-(2,3-difluoro-4-butylphenyl)dihydrobenzene
1-(Trans-4-octylcyclohexyl)-4-(2,3-difluoro-4-pentylphenyl)dihydrobenzene
1- (Trans-4-octylcyclohexyl) -4- (2,3-difluoro-4-octylphenyl)dihydrobenzene
1-(Trans-4-octylcyclohexyl)-4-(2,3-difluoro-4-decylphenyl)dihydrobenzene
1-(Trans-4-decylcyclohexyl)-4-(2,3-difluoro-4-methylphenyl)dihydrobenzene
1-(Trans-4-decylcyclohexyl)-4-(2,3-difluoro-4-butylphenyl)dihydrobenzene
1-(Trans-4-decylcyclohexyl)-4-(2,3-difluoro-4-pentylphenyl)dihydrobenzene
1-(Trans-4-decylcyclohexyl)-4-(2,3-difluoro-4-octylphenyl)dihydrobenzene
1- (Trans-4-decylcyclohexyl) -4- (2,3-difluoro-4 -decylphenyl ) dihydrobenzene

EXAMPLE 26

A solution of 30.1 g of 3,5-difluorobromobenzene in 90 ml of anhydrous diethyl ether was added dropwise under stirring at 15°–20° C. to 4.5 g of magnesium metal powder, followed by reaction at room temperature for one hour so that 3,5-difluoromagnesium bromobenzene (a Grignard reagent) was formed. After 20 g of 4-pentylcyclohexenone were added under stirring at −10° to 0° C. to the thus-formed Grignard reagent, they were reacted at room temperature for additional 1 hour. After the completion of the reaction, diluted hydrochloric acid was gradually added dropwise to the reaction mixture, followed by extraction with diethyl ether. After the extract was washed with saturated NaCl, anhydrous sodium sulfate was added to dry the extract. The resultant mixture was filtered and the solvent was distilled off from the filtrate under reduced pressure, whereby 1-(1-hydroxy-4-pentylcyclohexenyl)-3,5-difluorobenzene was obtained as a crude reaction product.

The crude reaction product was dissolved in 250 ml of toluene. After 0.5 g of p-toluenesulfonic acid monohydrate was added to the resultant solution, the mixture thus obtained was refluxed under stirring. During the reflux, water which was formed by the reaction was removed by a decanter. The dehydration reaction was conducted for 30 minutes and the reaction mixture was then cooled. The toluene layer was washed successively with saturated $Na_2CO_3$ and then with saturated NaCl, and was then dried over anhydrous sodium sulfate. The toluene was thereafter distilled off under reduced pressure. The residue was next purified by distillation under reduced pressure, whereby 24 g of 1-(4-pentyldihydrophenyl)-3,5-difluorobenzene were obtained.

The compound so obtained had a melting point of −31° C.

The following compounds can be prepared in a similar manner.

1-(4-Methyldihydrophenyl)-3,5-difluorobenzene
1-(4-Ethyldihydrophenyl)-3,5-difluorobenzene
1-(4-Propyldihydrophenyl)-3,5-difluorobenzene
1-(4-Butyldihydrophenyl)-3,5-difluorobenzene
1-(4-Hexyldihydrophenyl)-3,5-difluorobenzene
1-(4-Heptyldihydrophenyl)-3,5-difluorobenzene
1-(4-Octyldihydrophenyl)-3,5-difluorobenzene
1-(4-Nonyldihydrophenyl)-3,5-difluorobenzene
1-(4-Decyldihydrophenyl)-3,5-difluorobenzene

EXAMPLE 27

In a similar manner to Example 26 except for the replacement of 20 g of 4-pentylcyclohexenone, one of the raw materials in Example 26, by 30 g of trans-4-pentylcyclohexylcyclohexenone, 31 g of 1-(trans-4-pentylcyclohexyldihydrophenyl)-3,5-difluorobenzene were obtained.

The compound so obtained was a nematic liquid crystal having C-N and N-I points at 36° C. and 75° C., respectively.

The following compounds can also be prepared in a similar manner.

1-(Trans-4-methylcyclohexyldihydrophenyl)-3,5-difluorobenzene
1-(Trans-4-ethylcyclohexyldihydrophenyl)-3,5-difluorobenzene
1-(Trans-4-propylcyclohexyldihydrophenyl)-3,5-difluorobenzene
1-(Trans-4-butylcyclohexyldihydrophenyl)-3,5-difluorobenzene
1-(Trans-4-hexylcyclohexyldihydrophenyl)-3,5-difluorobenzene
1-(Trans-4-heptylcyclohexyldihydrophenyl)-3,5-difluorobenzene
1-(Trans-4-octylcyclohexyldihydrophenyl)-3,5-difluorobenzene
1-(Trans-4-nonylcyclohexyldihydrophenyl)-3,5-difluorobenzene
1-(Trans-4-decylcyclohexyldihydrophenyl)-3,5-difluorobenzene

EXAMPLE 28

In anhydrous tetrahydrofuran (40 ml), 10.5 g of the 1-(4-pentyldihydrophenyl)-3,5-difluorobenzene, which had been obtained in Example 26, were dissolved. The resulting solution was cooled to −70° C., to which 27 ml of a solution of n-butyllithium in hexane (1.5 mol/l) were added dropwise. After the completion of the dropwise addition, the resulting solution was reacted at −50° C. for additional 5 hours, whereby 1-(4-pentyldihydrophenyl)-3,5-difluoro-4-lithiumbenzene was formed. The product so obtained was cooled to −70° C., to which 2 g of solid $CO_2$ were added. They were heated to room temperature under stirring and reacted. After the completion of the reaction, diluted hydrochloric acid was gradually added dropwise, followed by extraction with diethyl ether. After the extract was washed with saturated NaCl, anhydrous sodium sulfate was added to dry the extract. The resultant mixture was filtered and the solvent was distilled off from the filtrate under reduced pressure. The reaction product so obtained was recrystallized from a mixed solvent of ethyl acetate and toluene, whereby 9.5 g of 4-(4-pentyl-dihydrophenyl)-2,6-difluorobenzoic acid were obtained.

The compound so obtained had a melting point of 65° C.

The following compounds can also be prepared in a similar manner.

4-(4-Methyldihydrophenyl)-2,6-difluorobenzoic acid
4-(4-Ethyldihydrophenyl)-2,6-difluorobenzoic acid
4-(4-Propyldihydrophenyl)-2,6-difluorobenzoic acid
4-(4-Butyldihydrophenyl)-2,6-difluorobenzoic acid
4-(4-Hexyldihydrophenyl)-2,6-difluorobenzoic acid
4-(4-Heptyldihydrophenyl)-2,6-difluorobenzoic acid
4-(4-Octyldihydrophenyl)-2,6-difluorobenzoic acid
4-(4-Nonyldihydrophenyl)-2,6-difluorobenzoic acid
4-(4-Decyldihydrophenyl)-2,6-difluorobenzoic acid

EXAMPLE 29

In 20 ml of methylene chloride, 3.7 g of the 4-(4-pentyldihydrophenyl)-2,6-difluorobenzoic acid, which had been obtained in Example 28, and 1.19 g of 4-cyanophenol were dissolved. To the resulting solution, 2.47 g of N,N'-dicyclohexylcarbodiimide were added, followed by stirring at room temperature for 3 hours. After the completion of the reaction, crystals precipitated were filtered off and the filtrate was passed through a silica gel column to purify the same. The methylene chloride was distilled off under reduced pressure, whereby 3.5 g of 4-cyanophenyl 4-(4-pentyl-dihydrophenyl)-2,6-difluorobenzoate were obtained.

The compound so obtained was a nematic liquid crystal having C-N and N-I points at 81° C. and 176° C., respectively.

The following compounds can also be prepared in a similar manner.

4-Cyanophenyl 4-(4-methyldihydrophenyl)-2,6-difluorobenzoate
4-Cyanophenyl 4-(4-ethyldihydrophenyl)-2,6-difluorobenzoate
4-Cyanophenyl 4-(4-propyldihydrophenyl)-2,6-difluorobenzoate
4-Cyanophenyl 4-(4-butyldihydrophenyl)-2,6-difluorobenzoate

| | |
|---|---|
| 4-Cyanophenyl difluorobenzoate | 4-(4-hexyldihydrophenyl)-2,6- |
| 4-Cyanophenyl difluorobenzoate | 4-(4-heptyldihydrophenyl)-2,6- |
| 4-Cyanophenyl difluorobenzoate | 4-(4-octyldihydrophenyl)-2,6- |
| 4-Cyanophenyl difluorobenzoate | 4-(4-nonyldihydrophenyl)-2,6- |
| 4-Cyanophenyl difluorobenzoate | 4-(4-decyldihydrophenyl )-2,6- |

EXAMPLE 30

In a similar manner to Example 29 except for the replacement of 1.19 g of 4-cyanophenol, one of the raw materials in Example 29, by 1.14 g of 4-fluorophenol, 3.2 g of 4-(4-pentyldihydrophenyl)-2,6-fluorobenzoate were obtained.

The compound so obtained was a nematic liquid crystal having C-N and N-I points at 64° C. and 100° C., respectively.

The following compounds can also be prepared in a similar manner.

| | |
|---|---|
| 4-Fluorophenyl difluorobenzoate | 4-(4-methyldihydrophenyl)-2,6- |
| 4-Fluorophenyl difluorobenzoate | 4-(4-ethyldihydrophenyl)-2,6- |
| 4-Fluorophenyl difluorobenzoate | 4-(4-propyldihydrophenyl)-2,6- |
| 4-Fluorophenyl difluorobenzoate | 4-(4-butyldihydrophenyl)-2,6- |
| 4-Fluorophenyl difluorobenzoate | 4-(4-hexyldihydrophenyl)-2,6- |
| 4-Fluorophenyl difluorobenzoate | 4-(4-heptyldihydrophenyl)-2,6- |
| 4-Fluorophenyl difluorobenzoate | 4-(4-octyldihydrophenyl)-2,6- |
| 4-Fluorophenyl difluorobenzoate | 4-(4-nonyldihydrophenyl)-2,6- |
| 4-Fluorophenyl difluorobenzoate | 4-(4-decyldihydrophenyl)-2,6- |

EXAMPLE 31

In anhydrous tetrahydrofuran (40 ml), 3.4 g of the 1-(4-pentyldihydrophenyl)-3,5-difluorobenzene, which had been obtained in Example 26, were dissolved. The resulting solution was cooled to −70° C., to which 6.7 ml of a solution of n-butyllithium in hexane (1.5 mol/l) were added dropwise. After the completion of the dropwise addition, the resulting solution was reacted at −50° C. for additional 5 hours, whereby 1-(4-pentylcyclohexenyl)-3,5-difluoro-4-lithiumbenzene was formed. The product so obtained was cooled to −70° C., to which a solution of 1.1 g of potassium tert-butoxide in 20 ml of anhydrous tetrahydrofuran was added dropwise under stirring over one hour. After the completion of the dropwise addition, the resulting mixture was stirred at the same temperature for 10 minutes, followed by the dropwise addition of a solution of 1.71 g of iodohexane in 5 ml of anhydrous tetrahydrofuran under stirring. After the completion of the dropwise addition, they were heated to room temperature under stirring and reacted. After the completion of the reaction, diluted hydrochloric acid was gradually added dropwise to the reaction mixture, followed by extraction with diethyl ether. After the extract was washed successively with saturated NaHSO$_3$, saturated Na$_2$CO$_3$ and saturated NaCl, anhydrous sodium sulfate was added to dry the extract. The resultant mixture was filtered and the solvent was distilled off from the filtrate under reduced pressure. The reaction product was recrystallized from a mixed solvent of ethyl acetate and ethanol, whereby 3.5 g of 1-(4-pentyldihydrophenyl)-3,5-difluoro-4-hexylbenzene were obtained.

The compound so obtained had a melting point of 35° C.

The following compounds can also be prepared in a similar manner.

4-(4-Methyldihydrophenyl)-3,5-difluoro-4-methylbenzene
4-(4-Methyldihydrophenyl)-3,5-difluoro-4-butylbenzene
4-(4-Methyldihydrophenyl)-3,5-difluoro-4-pentylbenzene
4-(4-Methyldihydrophenyl)-3,5-difluoro-4-octylbenzene
4-(4-Methyldihydrophenyl)-3,5-difluoro-4-decylbenzene
4-(4-Propyldihydrophenyl)-3,5-difluoro-4-methylbenzene
4-(4-Propyldihydrophenyl)-3,5-difluoro-4-butylbenzene
4-(4-Propyldihydrophenyl)-3,5-difluoro-4-pentylbenzene
4-(4-Propyldihydrophenyl)-3,5-difluoro-4-octylbenzene
4-(4-Propyldihydrophenyl)-3,5-difluoro-4-decylbenzene
4-(4-Hexyldihydrophenyl)-3,5-difluoro-4-methylbenzene
4-(4-Hexyldihydrophenyl)-3,5-difluoro-4-butylbenzene
4-(4-Hexyldihydrophenyl)-3,5-difluoro-4-pentylbenzene
4-(4-Hexyldihydrophenyl)-3,5-difluoro-4-octylbenzene
4-(4-Hexyldihydrophenyl)-3,5-difluoro-4-decylbenzene
4-(4-Octyldihydrophenyl)-3,5-difluoro-4-methylbenzene
4-(4-Octyldihydrophenyl)-3,5-difluoro-4-butylbenzene
4-(4-Octyldihydrophenyl)-3,5-difluoro-4-pentylbenzene
4-(4-Octyldihydrophenyl)-3,5-difluoro-4-octylbenzene
4-(4-Octyldihydrophenyl)-3,5-difluoro-4-decylbenzene
4-(4-Decyldihydrophenyl)-3,5-difluoro-4-methylbenzene
4-(4-Decyldihydrophenyl)-3,5-difluoro-4-butylbenzene
4-(4-Decyldihydrophenyl)-3,5-difluoro-4-pentylbenzene
4-(4-Decyldihydrophenyl)-3,5-difluoro-4-octylbenzene
4-(4-Decyldihydrophenyl)-3,5-difluoro-4-decylbenzene

EXAMPLE 32

In 20 ml of thionyl chloride, 2.8 g of the 4-(4-pentyldihydrophenyl)-2,6-difluorobenzoic acid, which had been obtained in Example 28, were dissolved, followed by reflux under stirring for 2 hours. The thionyl chloride was then distilled off under reduced pressure. Aqueous ammonia was added, followed by stirring at 10° C. for 30 minutes. After the completion of the reaction, crystals precipitated were collected by filtration and recrystallized from a mixed solvent of ethyl acetate and ethanol, whereby 4-(4-pentyldihydrophenyl)-2,6-difluorobenzoic acid amide was obtained. The compound so obtained was dissolved in 15 ml of thionyl chloride, followed by reflux under stirring for 2 hours. The thionyl chloride was thereafter distilled off under reduced pressure. The residue was recrystallized from a mixed solvent of ethyl acetate and ethanol, whereby 1 g of 4-(4-pentyldihydrophenyl)-2,6-difluorocyanobenzene was obtained.

The compound so obtained had a melting point of 59° C.

The following compounds can be prepared in a similar manner.

4-(4-Methyldihydrophenyl)-2,6-difluorocyanobenzene
4-(4-Ethyldihydrophenyl)-2,6-difluorocyanobenzene
4-(4-Propyldihydrophenyl)-2,6-difluorocyanobenzene
4-(4-Butyldihydrophenyl)-2,6-difluorocyanobenzene
4-(4-Hexyldihydrophenyl)-2,6-difluorocyanobenzene
4-(4-Heptyldihydrophenyl)-2,6-difluorocyanobenzene
4-(4-Octyldihydrophenyl)-2,6-difluorocyanobenzene
4-(4-Nonyldihydrophenyl)-2,6-difluorocyanobenzene
4-(4-Decyldihydrophenyl)-2,6-difluorocyanobenzene

EXAMPLE 33

In anhydrous tetrahydrofuran (15 ml), 3.4 g of the 1-(trans-4-pentylcyclohexyldihydrophenyl)-3,5-difluorobenzene, which had been obtained in Example 27, were dissolved. The resulting solution was cooled to −70° C., to which 6.7 ml of a solution of n-butyllithium in hexane (1.5 mol/l) were added dropwise. After the completion of the dropwise addition, the resulting solution was reacted at −50° C. for additional 5 hours, whereby 1-[4-(trans-4-pentylcyclohexyl)-dihydrophenyl]-3,5-difluoro-4-lithiumbenzene was formed. The product so obtained was cooled to −70° C., to which a solution of 1.1 g of potassium tert-butoxide in 20 ml of anhydrous tetrahydrofuran was added dropwise over one hour. After the completion of the dropwise addition, the resulting mixture was stirred at the same temperature for 10 minutes, followed by the addition of a solution of 1.71 g of iodoethane in 10 ml of anhydrous tetrahydrofuran under stirring. After the completion of the dropwise addition, they were heated to room temperature under stirring and reacted.

After the completion of the reaction, diluted hydrochloric acid was gradually added dropwise to the reaction mixture, followed by extraction with diethyl ether. After the extract was washed successively with saturated NaHSO₃, saturated Na₂CO₃ and saturated NaCl, anhydrous sodium sulfate was added to dry the extract. The resultant mixture was filtered and the solvent was distilled off from the filtrate under reduced pressure. The reaction product was recrystallized from a mixed solvent of ethyl acetate and ethanol, whereby 2.8 g of 1-[4-(trans-4-pentylcyclohexyl)-dihydrophenyl]-3,5-difluoro-4-ethylbenzene were obtained.

The compound so obtained was a liquid crystal having C-S, S-N and N-I points at 32° C., 78° C. and 102° C., respectively.

The following compounds can also be prepared in a similar manner.

1-[4-(Trans-4-methylcyclohexyl)-dihydrophenyl]-3,5-difluoro-4-methylbenzene
1-[4-(Trans-4-methylcyclohexyl)-dihydrophenyl]-3,5-difluoro-4-butylbenzene
1-[4-(Trans-4-methylcyclohexyl)-dihydrophenyl]-3,5-difluoro-4-pentylbenzene
1-[4-(Trans-4-methylcyclohexyl)-dihydrophenyl]-3,5-difluoro-4-octylbenzene
1-[4-(Trans-4-methylcyclohexyl)-dihydrophenyl]-3,5-difluoro-4-decylbenzene
1-[4-(Trans-4-propylcyclohexyl)-dihydrophenyl]-3,5-difluoro-4-methylbenzene
1-[4-(Trans-4-propylcyclohexyl)-dihydrophenyl]-3,5-difluoro-4-butylbenzene
1-[4-(Trans-4-propylcyclohexyl)-dihydrophenyl]-3,5-difluoro-4-pentylbenzene
1-[4-(Trans-4-propylcyclohexyl)-dihydrophenyl]-3,5-difluoro-4-octylbenzene
1-[4-(Trans-4-propylcyclohexyl)-dihydrophenyl]-3,5-difluoro-4-decylbenzene
1-[4-(Trans-4-hexylcyclohexyl)-dihydrophenyl]-3,5-difluoro-4-methylbenzene
1-[4-(Trans-4-hexylcyclohexyl)-dihydrophenyl]-3,5-difluoro-4-butylbenzene
1-[4-(Trans-4-hexylcyclohexyl)-dihydrophenyl]-3,5-difluoro-4-pentylbenzene
1-[4-(Trans-4-hexylcyclohexyl)-dihydrophenyl]-3,5-difluoro-4-octylbenzene
1-[4-(Trans-4-hexylcyclohexyl)-dihydrophenyl]-3,5-difluoro-4-decylbenzene
1-[4-(Trans-4-octylcyclohexyl)-dihydrophenyl]-3,5-difluoro-4-methylbenzene
1-[4-(Trans-4-octylcyclohexyl)-dihydrophenyl]-3,5-difluoro-4-butylbenzene
1-[4-(Trans-4-octylcyclohexyl)-dihydrophenyl]-3,5-difluoro-4-pentylbenzene
1-[4-(Trans-4-octylcyclohexyl)-dihydrophenyl]-3,5-difluoro-4-octylbenzene
1-[4-(Trans-4-octylcyclohexyl)-dihydrophenyl]-3,5-difluoro-4-decylbenzene
1-[4-(Trans-4-decylcyclohexyl)-dihydrophenyl]-3,5-difluoro-4-methylbenzene
1-[4-(Trans-4-decylcyclohexyl)-dihydrophenyl]-3,5-difluoro-4-butylbenzene
1-[4-(Trans-4-decylcyclohexyl)-dihydrophenyl]-3,5-difluoro-4-pentylbenzene
1-[4-(Trans-4-decylcyclohexyl)-dihydrophenyl]-3,5-difluoro-4-octylbenzene
1-[4-(Trans-4-decylcyclohexyl)-dihydrophenyl]-3,5-difluoro-4-decylbenzene

EXAMPLE 34

A solution of 6.4 g of 3,4,5-trifluorobromobenzene in 30 ml of anhydrous diethyl ether was added dropwise under stirring at 10°–15° C. to 0.66 g of magnesium metal powder, followed by reaction at room temperature for 1 hour so that a Grignard reagent was formed. After 5 g of trans-4-butylcyclohexylhexenone were added dropwise under stirring at −10° to 0° C. to the thus-formed Grignard reagent, they were reacted at room temperature for additional 1 hour. After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 1-[1-hydroxy-4-(trans-4-butyl-cyclohexenyl)-cyclohexenyl]-3,4,5-trifluorobenzene was obtained as a crude reaction product.

The crude reaction product was dissolved in 50 ml of toluene. After 0.05 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated Na$_2$CO$_3$ and then with saturated NaCl, and was then dried over anhydrous sodium sulfate. The toluene was thereafter distilled off under reduced pressure. The reaction product so obtained was recrystallized twice from ethanol, whereby 1.2 g of 1-[4-(trans-4-butylcyclohexyl)-dihydrophenyl]-3,4,5-trifluorobenzene were obtained.

The compound so obtained was a monotropic liquid crystal having a melting point of 60° C. and an I-N point of 59° C.

The following compounds can be prepared in a similar manner.

1-[4-(Trans-4-methylcyclohexyl)-dihydrophenyl]-3,4,5-trifluorobenzene
1-[4-(Trans-4-ethylcyclohexyl)-dihydrophenyl]-3,4,5-trifluorobenzene
1-[4-(Trans-4-propylcyclohexyl)-dihydrophenyl]-3,4,5-trifluorobenzene
1-[4-(Trans-4-pentylcyclohexyl)-dihydrophenyl]-3,4,5-trifluorobenzene
1-[4-(Trans-4-hexylcyclohexyl)-dihydrophenyl]-3,4,5-trifluorobenzene
1-[4-(Trans-4-heptylcyclohexyl)-dihydrophenyl]-3,4,5-trifluorobenzene
1-[4-(Trans-4-octylcyclohexyl)-dihydrophenyl]-3,4,5-trifluorobenzene
1-[4-(Trans-4-nonylcyclohexyl)-dihydrophenyl]-3,4,5-trifluorobenzene
1-[4-(Trans-4-decylcyclohexyl)-dihydrophenyl]-3,4,5-trifluorobenzene

EXAMPLE 35

A solution of 6.4 g of 3,4,5-trifluorobromobenzene in 30 ml of anhydrous diethyl ether was added dropwise under stirring at 10°-15° C. to 0.66 g of magnesium metal powder, followed by reaction at room temperature for 1 hour so that a Grignard reagent was formed. After 4.0 g of 4-heptylcyclohexenone were added under stirring at −10° to 0° C. to the thus-formed Grignard reagent, they were reacted at room temperature for additional 1 hour.

After the completion of the reaction, diluted hydrochloric acid was added dropwise to the reaction mixture, followed by the extraction of the reaction mixture with diethyl ether. After the extract was washed with saturated NaCl, anhydrous sodium sulfate was added to dry the extract. The diethyl ether was distilled off under reduced pressure, whereby 1-(1-hydroxy-4-heptylcyclohexenyl)-3,4,5-trifluorobenzene was obtained as a crude reaction product. The crude reaction product was dissolved in 50 ml of toluene. After 0.05 g of p-toluenesulfonic acid monohydrate was added to the resultant solution, the mixture thus obtained was refluxed under stirring. During the reflux, water which was formed by the reaction was removed by a decanter. The dehydration reaction was conducted for 1 hour and the reaction mixture was then cooled. The toluene layer was washed successively with saturated Na$_2$CO$_3$ and then with saturated NaCl, and was then dried over anhydrous sodium sulfate. The toluene was thereafter distilled off under reduced pressure. The reaction product so obtained was recrystallized twice from ethanol, whereby 1.0 g of 1-(4-heptyldihydrophenyl)-3,4,5-trifluorobenzene was obtained.

The compound so obtained had a melting point of 14° C.

The following compounds can be prepared in a similar manner.

1-(4 -Methyldihydrophenyl)-3,4,5-trifluorobenzene
1-(4 -Ethyldihydrophenyl) -3,4,5-trifluorobenzene
1-(4 -Propyldihydrophenyl)-3,4,5-trifluorobenzene
1-(4 -Butyldihydrophenyl) -3,4,5-trifluorobenzene
1-(4 -Pentyldihydrophenyl)-3,4,5-trifluorobenzene
1-(4 -Hexyldihydrophenyl)-3,4,5-trifluorobenzene
1-(4 -Octyldihydrophenyl)-3,4,5-trifluorobenzene
1-(4 -Nonyldihydrophenyl)-3,4,5-trifluorobenzene
1-(4 -Decyldihydrophenyl)-3,4,5-trifluorobenzene

EXAMPLE 36

A liquid crystal composition consisting of 44.5 % of 1-(trans-4-propylcyclohexyl)-4-(3,4-difluorophenyl)-dihydrobenzene, 44.5% of 1-(trans-4-butylcyclohexyl)-4-(3,4-difluorophenyl)dihydrobenzene and 11% of 1-pentyl-4-(3,4-difluorophenyl)dihydrobenzene, all of which are compounds according to this invention, was prepared, and its characteristics as a liquid crystal was investigated. The results are shown below. $V_{th}$ is the operating threshold voltage of the liquid crystal composition as sealed in a TN (twisted nematic) liquid crystal display having a cell thickness of 9 μm.

Characteristics of the Liquid Crystal Composition

N-I Point: 84° C.
Viscosity: 28 cps
Δn (20° C.): 0.137
Δε (25° C.): 6.5
$V_{th}$ (25° C.): 1.80 V

EXAMPLE 37

Liquid crystal compositions were each prepared by mixing 10 parts by weight of the corresponding compound of this invention with 90 parts by weight of a liquid crystal composition (mixed liquid crystal composition) which had in turn been prepared by mixing the below described compounds. Characteristics of the liquid crystal compositions are presented in Tables 2-1 and 2-2, in which $V_{th}$ is the operating threshold voltage of each liquid crystal composition as sealed in a TN (twisted nematic) liquid crystal display having a cell thickness of 9 μm.

Mixed Liquid Crystal Compositions

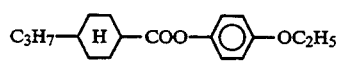

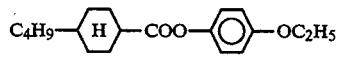

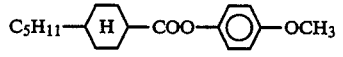

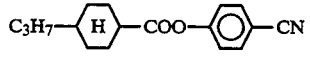

-continued

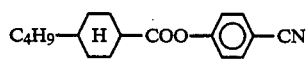

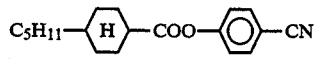

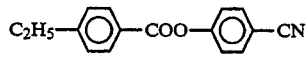

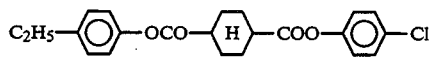

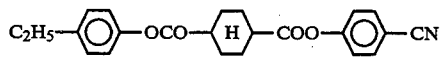

1. A liquid crystal composition comprising a 1,4-substituted dihydrobenzene derivative represented by the following formula (I):

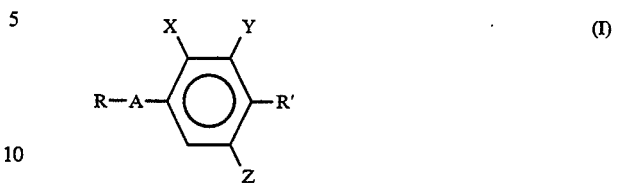

wherein A means a 1,4-dihydrophenylene group, R denotes a hydrogen atom or a $C_{1-10}$ alkyl, cyclohexyl or trans-4-$C_{1-10}$ alkylcyclohexyl group, R' represents a hydrogen or halogen atom, a trifluoromethyl, trifluoromethoxy, cyano, $C_{1-10}$ alkyl, $C_{1-10}$ alkoxy or carboxyl group or a group —COO—B—R", said B stand-

TABLE 2(1)

| Invention Compound | | | | | (Results) | | | |
|---|---|---|---|---|---|---|---|---|
| R | X | Y | Z | R' | N-I point | Δn (20° C.) | Visocisty (20° C., cps) | Vth (25° C., V) |
| $C_5H_{11}$— | H | H | H | F | 56° C. | 0.104 | 31.1 | 1.32 |
| $C_5H_{11}$—⟨H⟩— | H | H | H | F | 76° C. | 0.112 | 35.9 | 1.57 |
| $C_3H_7$—⟨H⟩— | H | F | H | F | 71° C. | 0.111 | 36.7 | 1.48 |
| $C_5H_{11}$— | H | H | H | CN | 64° C. | 0.116 | 36.8 | 1.38 |
| $C_3H_7$—⟨H⟩— | H | H | H | $CH_3$ | 81° C. | 0.118 | 34.4 | 1.71 |
| $C_5H_{11}$— | H | F | H | F | 49° C. | 0.100 | 32.9 | 1.26 |

TABLE 2(2)

| Invention Compound | | | | | (Results) | | | |
|---|---|---|---|---|---|---|---|---|
| R | X | Y | Z | R' | N-I point | Δn (20° C.) | Visocisty (20° C., cps) | Vth (25° C., V) |
| $C_3H_7$—⟨H⟩— | H | F | H | H | 68° C. | 0.109 | 35.0 | 1.61 |
| $C_3H_7$—⟨H⟩— | F | F | H | $C_2H_5$ | 72° C. | 0.111 | 35.9 | 1.59 |
| $C_5H_{11}$— | H | F | F | H | 51° C. | 0.094 | 33.7 | 1.37 |
| $C_7H_{15}$— | H | F | F | F | 54° C. | 0.100 | 34.0 | 1.32 |
| Mixed liquid crystal composition (control) | | | | | 67° C. | 0.106 | 37.0 | 1.50 |

As is understood from these tables, the compounds according to the present invention provide low-viscosity liquid crystal compositions and, moreover, lower the threshold voltage or raise the N-I point without impairment of other characteristics.

We claim:

ing for an unsubstituted or halogen-substituted 1,4-phenylene or 1,4-cyclohexenylene group and said R" representing a halogen atom or a cyano, $C_{1-10}$ alkyl or $C_{1-10}$ alkoxy group, and X, Y and Z individually means a hydrogen or halogen atom, with the proviso that:

R' is other than a hydrogen or chlorine atom or a cyano or methyl group when R is a hydrogen atom and X, Y and Z are each a hydrogen atom, R' is other than a hydrogen atom when R is a $C_{1-10}$ alkyl group and X, Y and Z are each a hydrogen atom, and X, Y and Z are each other than a chlorine atom when R is a hydrogen atom and R' is a hydrogen atom.

2. A liquid crystal display comprising a combination of cells opposing each other, each of said cells being composed of a transparent plate and transparent electrodes formed thereon, and a liquid crystal composition composed of a 1,4-substituted dihydrobenzene derivative represented by the following formula (I):

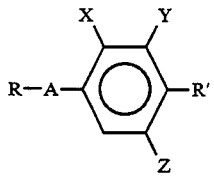

wherein A means a 1,4-dihydrophenylene group, R denotes a hydrogen atom or a $C_{1-10}$ alkyl, cyclohexyl or trans-4-$C_{1-10}$ alkylcyclohexyl group, R' represents a hydrogen or halogen atom, a trifluoromethyl, trifluoromethoxy, cyano, $C_{1-10}$ alkyl, $C_{1-10}$ alkoxy or carboxyl group or a group —COO—B—R", said B standing for an unsubstituted or halogen-substituted 1,4-phenylene or 1,4-cyclohexenylene group and said R" representing a halogen atom or a cyano, $C_{1-10}$ alkyl or $C_{1-10}$ alkoxy group, and X, Y and Z individually mean a hydrogen or halogen atom, with the proviso that:

R' is other than a hydrogen or chlorine atom or a cyano or methyl group when R is a hydrogen atom and X, Y and Z are each a hydrogen atom, R+ is other than a hydrogen atom when R is a $C_{1-10}$ alkyl group and X, Y and Z are each a hydrogen atom, and X, Y and Z are each other than a chlorine atom when R is a hydrogen atom and R' is a hydrogen atom, sealed between the cells.

* * * * *

UNITED STATES PATENT AND TRADEMARK OFFICE
CERTIFICATE OF CORRECTION

PATENT NO. : 5,342,546
DATED : August 30, 1994
INVENTOR(S) : Hisato SATO, et al.

It is certified that error appears in the above-indentified patent and that said Letters Patent is hereby corrected as shown below:

On the title page, Item[75], the last inventor's name should be spelled:

--Yasunobu Tsuji--

Signed and Sealed this

Thirty-first Day of January, 1995

*Attest:*

BRUCE LEHMAN

*Attesting Officer*   *Commissioner of Patents and Trademarks*